United States Patent
Takeda

(10) Patent No.: US 10,853,920 B2
(45) Date of Patent: Dec. 1, 2020

(54) IMAGE PROCESSING APPARATUS

(71) Applicant: SHIMADZU CORPORATION, Kyoto (JP)

(72) Inventor: Ryo Takeda, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 8 days.

(21) Appl. No.: 16/335,000

(22) PCT Filed: Sep. 21, 2016

(86) PCT No.: PCT/JP2016/077779
§ 371 (c)(1),
(2) Date: Mar. 20, 2019

(87) PCT Pub. No.: WO2018/055684
PCT Pub. Date: Mar. 29, 2018

(65) Prior Publication Data
US 2019/0266709 A1 Aug. 29, 2019

(51) Int. Cl.
G06T 5/00 (2006.01)
H04N 1/393 (2006.01)
H04N 1/409 (2006.01)
H04N 1/387 (2006.01)

(52) U.S. Cl.
CPC ............ G06T 5/002 (2013.01); G06T 5/00 (2013.01); H04N 1/387 (2013.01); H04N 1/393 (2013.01); H04N 1/409 (2013.01)

(58) Field of Classification Search
None
See application file for complete search history.

(56) References Cited

U.S. PATENT DOCUMENTS

| 5,561,724 | A | 10/1996 | Kido et al. |
| 5,602,934 | A | 2/1997 | Li et al. |
| 6,771,793 | B1 | 8/2004 | Yamada |
| 9,165,346 | B2 | 10/2015 | Fu et al. |
| 2010/0208992 | A1* | 8/2010 | Toyoda .................. G06T 5/002 382/167 |
| 2011/0080955 | A1* | 4/2011 | Shi ......................... G06T 7/223 375/240.16 |

(Continued)

FOREIGN PATENT DOCUMENTS

| JP | 3472596 A | 12/2003 |
| JP | 4244094 A | 3/2009 |
| JP | 2014-216019 A | 11/2014 |

OTHER PUBLICATIONS

Extended European Search Report dated Jan. 31, 2020, issued by the European Patent Office in Application No. 16916755.8.

(Continued)

Primary Examiner — Jiangeng Sun
(74) Attorney, Agent, or Firm — Sughrue Mion, PLLC

(57) ABSTRACT

An image processing apparatus (100) includes a synthetic image acquirer (24) for acquiring a plurality of smoothed images different from each other, in which noise components have been smoothed on an image to be processed, and that is operable to perform weighted synthesis of the smoothed images based on pixel value differences between a pixel value of a pixel of the image to be processed and pixel values of pixels of the acquired smoothed images, in which a positive and a negative have been taken into consideration.

6 Claims, 15 Drawing Sheets

(56) References Cited

U.S. PATENT DOCUMENTS

2014/0064632 A1\* 3/2014 Manabe .................. G06T 5/009
  382/254
2014/0133711 A1\* 5/2014 Abe ................... G06K 9/00067
  382/115

OTHER PUBLICATIONS

Written Opinion for PCT/JP2016/077779, dated Nov. 8, 2016.
International Search Report for PCT/JP2016/077779, dated Nov. 8, 2016.

\* cited by examiner

FIRST EMBODIMENT

EXAMPLE OF SMOOTHING FILTERS IN MATRIX OF 5 ROWS AND 5 COLUMNS
HAVING EIGHT SMOOTHING DIRECTIONS (AT INTERVALS OF 45 DEGREES)

*FIG.4*
EXAMPLE OF SMOOTHING FILTERS IN MATRIX OF 5 ROWS AND 5 COLUMNS
HAVING TWENTY-FOUR SMOOTHING DIRECTIONS (AT INTERVALS OF 15 DEGREES)
0-DEGREE DIRECTION
SMOOTHING FILTER
d = 1
15-DEGREE DIRECTION
SMOOTHING FILTER
d = 2
30-DEGREE DIRECTION
SMOOTHING FILTER
d = 3
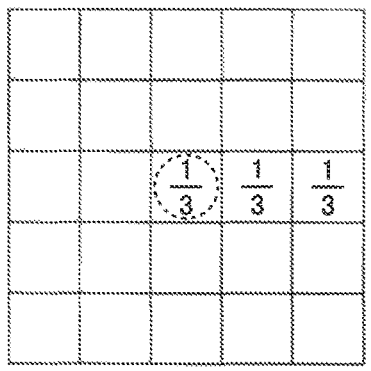
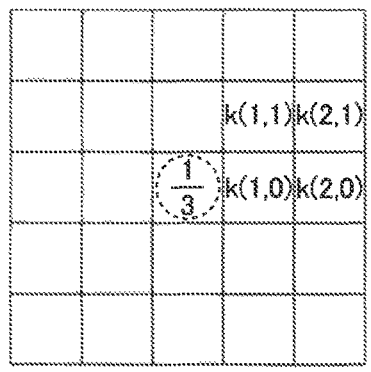
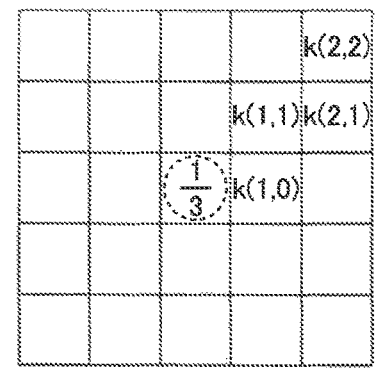
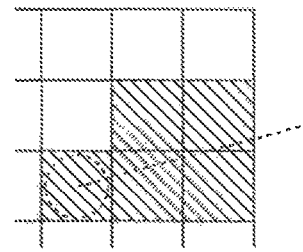
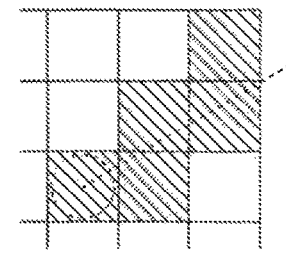
$\theta$ = 15 (DEGREES)  $\theta$ = 30 (DEGREES)
⋮
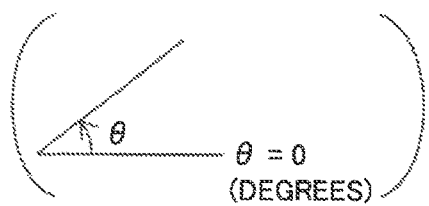
$\theta$ = 0 (DEGREES)

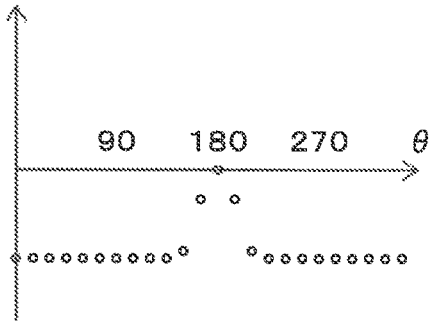
PIXEL VALUE DIFFERENCE
S(d)

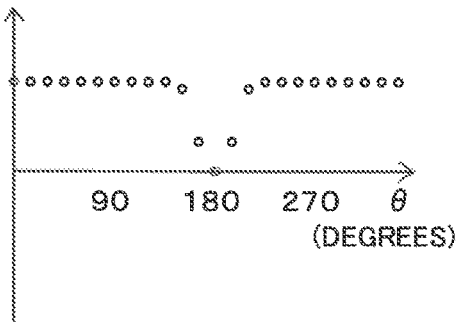
ABSOLUTE VALUE OF
PIXEL VALUE DIFFERENCE
|S(d)|

(2)

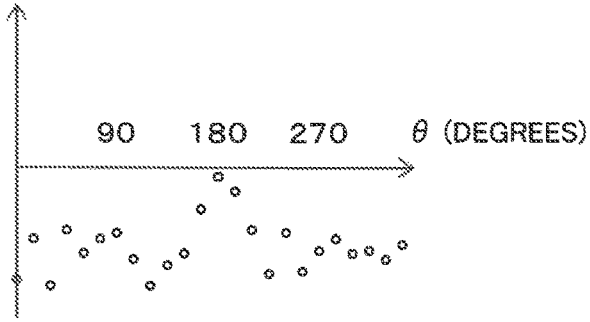
PIXEL VALUE DIFFERENCE
S(d)

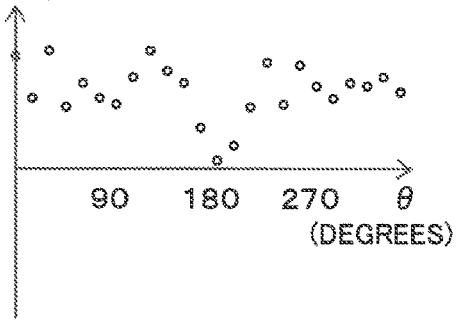
ABSOLUTE VALUE OF
PIXEL VALUE DIFFERENCE
|S(d)|

(3)

PIXEL VALUE DIFFERENCE S(d)

EVEN WHEN NOISE COMPONENTS ARE PRESENT AND PIXEL VALUE DIFFERENCE DEVIATES FROM 0, PIXEL VALUE DIFFERENCE IN DIRECTION ALONG STRUCTURE CAN BE DETERMINED FROM OVERALL TREND

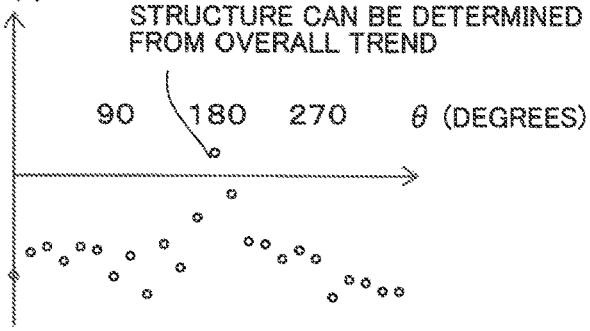

ABSOLUTE VALUE OF
PIXEL VALUE DIFFERENCE
|S(d)|

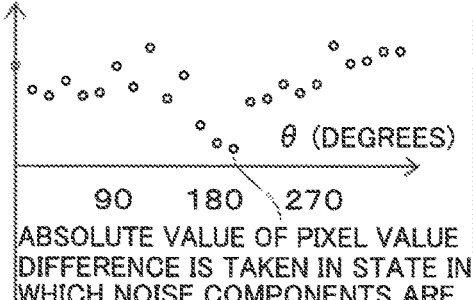

ABSOLUTE VALUE OF PIXEL VALUE DIFFERENCE IS TAKEN IN STATE IN WHICH NOISE COMPONENTS ARE PRESENT SUCH THAT SMOOTHING IN DIRECTION OF 195 DEGREES IS EMPHASIZED

FIG.14
(1) STEP FUNCTION
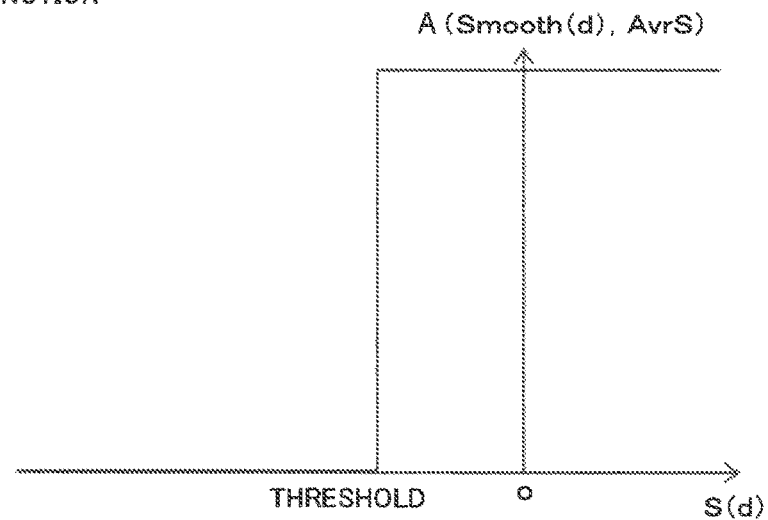
(2) LINEAR FUNCTION
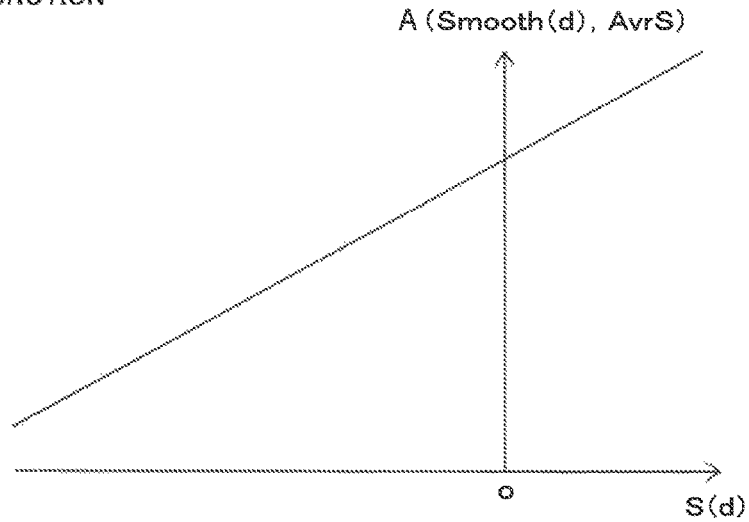
(3) LOGISTIC FUNCTION
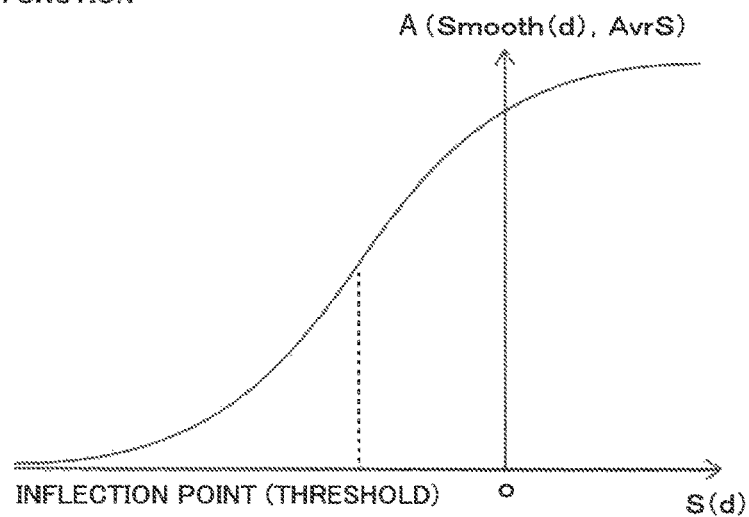

FIG.15
(1) STEP FUNCTION
B (In, Comp)
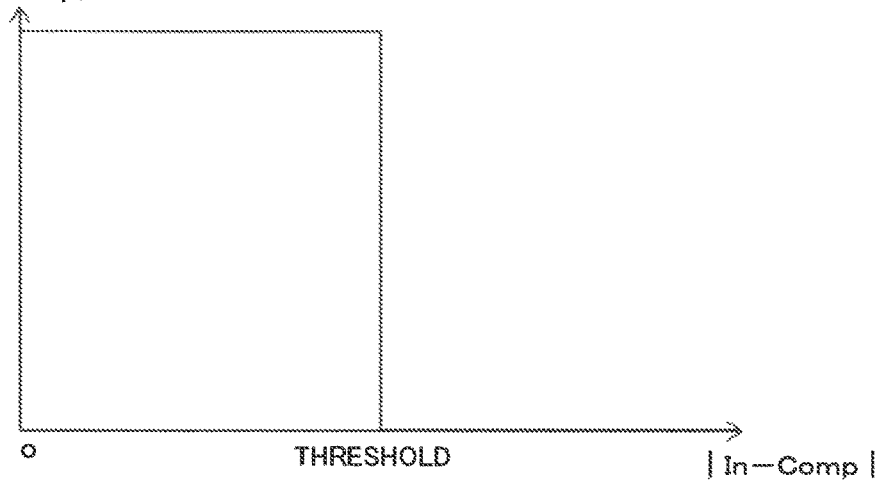
THRESHOLD    |In−Comp|
(2) LINEAR FUNCTION
B (In, Comp)
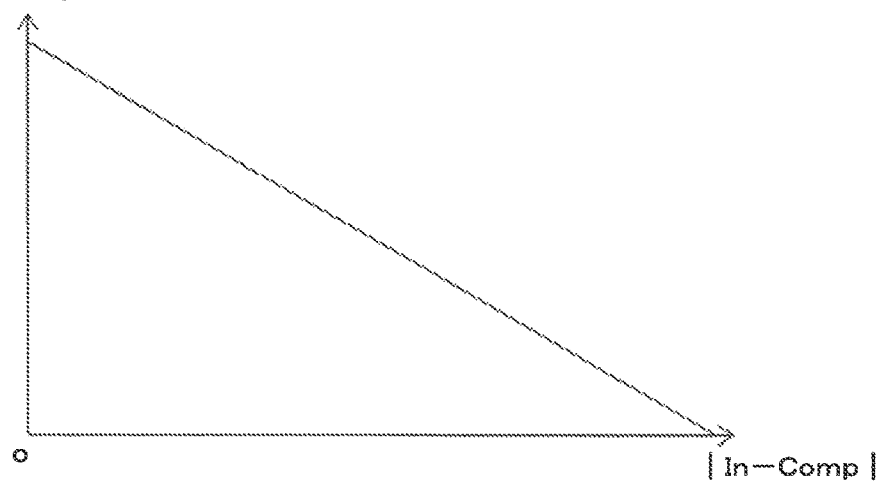
|In−Comp|
(3) LOGISTIC FUNCTION
B (In, Comp)
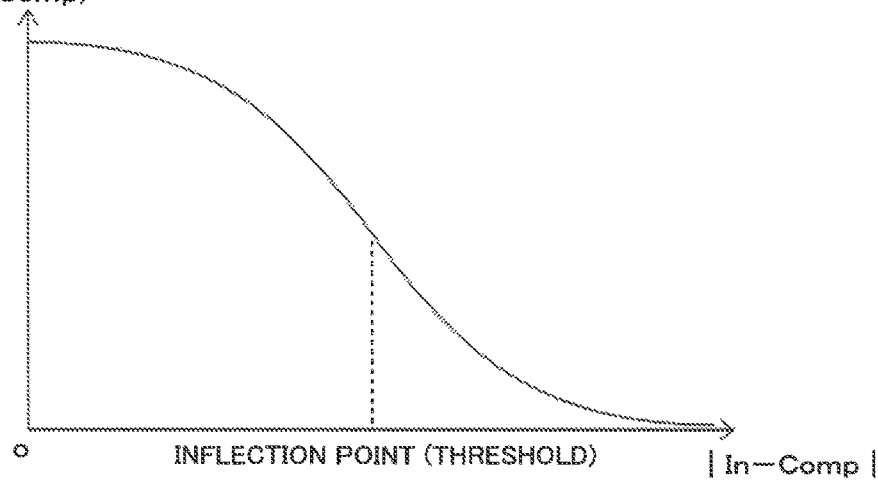
INFLECTION POINT (THRESHOLD)    |In−Comp|

IMAGE PROCESSING APPARATUS

CROSS REFERENCE TO RELATED APPLICATIONS

This Application is a National Stage of International Application No. PCT/JP2016/077779 filed Sep. 21, 2016.

The present invention relates to an image processing apparatus, and more particularly, it relates to an image processing apparatus that smoothes an image by a plurality of smoothing filters and synthesizes a plurality of smoothed images to generate an image with reduced noise components.

BACKGROUND ART

Conventionally, an image processing apparatus that smoothes an image by a plurality of smoothing filters and synthesizes a plurality of smoothed images to generate an image with reduced noise components is known. Such an image processing apparatus is disclosed in Japanese Patent No. 3472596, for example.

Japanese Patent No. 3472596 described above discloses a noise reduction filter (image processing apparatus) that acquires the pixel values of respective pixels of a plurality of smoothed images from a pixel value corresponding to luminance or chromaticity of each pixel of an image to be processed, using a plurality of smoothing filters different from each other and that smooth noise components for each pixel of the image to be processed, acquires the absolute values of pixel value differences between the pixel value of each pixel of the image to be processed and the pixel values of respective pixels at corresponding positions in the plurality of smoothed images for each of the plurality of smoothing filters, performs weighting of the plurality of smoothing filters based on the absolute values of the pixel value differences, and performs smoothing for each pixel. This noise reduction filter emphasizes a smoothing filter that performs smoothing in a direction in which there are many pixels with a small absolute value of the sum of differences of pixel values from the pixel value of a pixel of interest, and performs synthesis.

PRIOR ART

Patent Document

Patent Document 1: Japanese Patent No. 3472596

SUMMARY OF THE INVENTION

Problem to be Solved by the Invention

In the noise reduction filter (image processing apparatus) disclosed in Japanese Patent No. 3472596 described above, a smoothed image through the smoothing filter that performs smoothing in the direction in which there are many pixels with a small absolute value of the sum of the differences of the pixel values from the pixel value of the pixel of interest is emphasized, and synthesis is performed. Therefore, when noise components occur in the pixel values of image data, the absolute value of the difference between the pixel values increases or decreases from the value in the case in which there is no noise, and thus due to the noise, a smoothing filter different from that in the case in which there is no noise may be heavily weighted, and synthesis may be performed in some cases. In this case, there is a problem that it is difficult to appropriately smooth the image to be processed and perform synthesis.

The present invention has been proposed in order to solve the aforementioned problem, and an object of the present invention is to provide an image processing apparatus capable of performing image synthesis through appropriate smoothing even when noise components occur in the pixel values of image data.

Means for Solving the Problem

In order to attain the aforementioned object, an image processing apparatus according to an aspect of the present invention includes an image smoother for acquiring pixel values of respective pixels of a plurality of smoothed images from a pixel value corresponding to luminance or chromaticity of each pixel of an image to be processed, using a plurality of smoothing filters for smoothing noise components for the each pixel of the image to be processed, the plurality of smoothing filters being different from each other, a pixel value difference acquirer for acquiring pixel value differences between the pixel value of the each pixel of the image to be processed and the pixel values of the respective pixels at corresponding positions in the plurality of smoothed images, which are differences in the pixel values corresponding to the luminance or the chromaticity of the each pixel, in which a positive and a negative have been taken into consideration, for each of the plurality of smoothing filters, a synthesis weight acquirer for acquiring synthesis weights used for weighting to combine the pixel values of the respective pixels of the plurality of smoothed images, based on a plurality of the pixel value differences, and a synthetic image acquirer that is operable to perform weighted synthesis on the respective pixels of the plurality of smoothed images based on the synthesis weights of the pixel values of the respective pixels of the smoothed images to acquire a synthetic image.

As described above, the image processing apparatus according to this aspect of the present invention includes the synthesis weight acquirer that is operable to perform weighted synthesis based on the plurality of pixel value differences, in which a positive and a negative have been taken into consideration, between the pixel value of each pixel of the image to be processed and the pixel values of the respective pixels at the corresponding positions in the plurality of smoothed images to acquire the synthetic image. Accordingly, the overall trend of the pixel value differences in which a positive and a negative have been taken into consideration is considered to remain unchanged even when noise components occur, and thus unlike the case in which weighted synthesis of the smoothed images is performed based on the absolute values of the pixel value differences, the relationship of the pixel value differences is not reversed. Consequently, weighted synthesis of the smoothed images can be appropriately performed based on the pixel value differences in which a positive and a negative have been taken into consideration. Specifically, when the pixel value differences are close to 0, the pixel value differences fluctuate across a positive and a negative near 0 due to the influence of the noise components, and thus when the absolute values of the pixel value differences are taken, a distinction cannot be made when the overall trend is considered. On the other hand, when the positive and the negative of the pixel value differences are stored, the overall trend of the pixel value differences does not greatly change even if noise components are present, and thus an appropriate smoothed image can be selected to perform weighted synthesis. Thus, weighted synthesis of the smoothed images can be appropriately performed, and an appropriately smoothed image can be acquired.

In the aforementioned image processing apparatus according to this aspect, the synthesis weight acquirer preferably acquires an average value of the plurality of the pixel value differences in which a positive and a negative have been taken into consideration, and acquires a plurality of the synthesis weights corresponding to the each pixel based on the plurality of the pixel value differences and the average value of the pixel value differences. According to this structure, a smoothed image having an unusual pixel value difference can be easily found based on the average value, which is the overall trend of the pixel value differences, and thus weighted synthesis can be appropriately performed with the smoothed images based on the pixel value differences in which a positive and a negative have been taken into consideration, indicating changes due to smoothing for each of the smoothing filters.

In this case, when it is defined that the pixel value differences increase from a negative toward a positive, the synthesis weight acquirer is preferably operable to perform control of increasing a synthesis weight of a smoothed image corresponding to a smaller pixel value difference among the plurality of the pixel value differences for the each pixel when the average value of the pixel value differences is positive, and is preferable operable to perform control of increasing a synthesis weight of a smoothed image corresponding to a larger pixel value difference among the plurality of the pixel value differences for the each pixel when the average value of the pixel value differences is negative. According to this structure, when it is defined that the pixel value differences increase from a negative toward a positive, the smoothed image having an unusual pixel value difference can be easily found based on a smaller pixel value difference apart from the overall trend toward a negative when the average value of the pixel value differences is positive. Furthermore, when it is defined that the pixel value differences increase from a negative toward a positive, the smoothed image having an unusual pixel value difference can be easily found based on a larger pixel value difference apart from the overall trend toward a positive when the average value of the pixel value differences is negative. Therefore, a synthesis weight corresponding to the smoothed image having an unusual pixel value difference can be easily increased based on a pixel value difference at the peak position (unique position) relative to the average value of the pixel value differences. Consequently, the synthetic image obtained by more appropriately weighting the smoothed images according to the overall trend of the pixel value differences and performing synthesis can be acquired.

The aforementioned image processing apparatus according to this aspect preferably includes an additive synthetic image generator that is operable to perform weighted addition of the pixel value of the each pixel of the image to be processed and a pixel value of each pixel at a corresponding position in the synthetic image for the each pixel and is operable to perform synthesis to acquire an additive synthetic image. According to this structure, addition synthesis can be performed between the image to be processed and the synthetic image by further comparing the original image to be processed and the synthetic image, which is the result of smoothing, to consider the degree of change due to the smoothing.

In this case, the additive synthetic image generator preferably acquires an addition weight corresponding to the each pixel based on the pixel value of the each pixel of the image to be processed and the pixel value of the each pixel at the corresponding position in the synthetic image to acquire the additive synthetic image based on the addition weight when performing the weighted addition. According to this structure, the degree of weighting of addition of the image to be processed and the synthetic image can be easily acquired from the pixel value of each pixel of the image to be processed and the pixel value of each pixel at the corresponding position in the synthetic image.

The aforementioned image processing apparatus according to this aspect preferably further includes a band-limited image processor that is operable to perform frequency analysis on an input image to acquire a plurality of images subjected to band limitation, in which only images containing specific frequencies are extracted, for respective frequencies and is operable to perform frequency synthesis to merge again the plurality of images divided for the respective frequencies, and for acquiring an output image on which the frequency synthesis has been performed, and the band-limited image processor is preferably operable to perform the frequency analysis on the image to be processed as the input image to acquire the image to be processed, subjected to the band limitation, acquires the synthetic image subjected to the band limitation and the weighted synthesis based on the pixel value differences, in which a positive and a negative have been taken into consideration, for the each pixel, is preferably operable to perform the frequency synthesis on images based on the synthetic image subjected to the band limitation and the weighted synthesis, and preferably acquires the output image. According to this structure, the plurality of smoothed images are acquired for each frequency component of the image to be processed, weighted synthesis of the pixel value of each pixel of the image to be processed and the pixel values of the respective pixels at the corresponding positions in the plurality of smoothed images is performed based on the plurality of pixel value differences in which a positive and a negative have been taken into consideration, and the synthetic image is acquired such that the noise components can be smoothed for each frequency band. Consequently, weighted synthesis can be more effectively performed on image data obtained by smoothing noise components while blurring of the boundary of the structure of a subject reflected on the image is significantly reduced or prevented.

Effect of the Invention

As described above, according to the present invention, even when the noise components occur in the pixel values of the image data, the smoothed images are appropriately weighted such that image synthesis can be performed through appropriate smoothing.

BRIEF DESCRIPTION OF THE DRAWINGS

FIG. 4 is a diagram showing an example of smoothing filters of 5 rows and 5 columns that perform smoothing in line segment directions different from each other with a relationship of 15-degree intervals from the position of interest.

FIG. 6 is graphs plotting pixel value differences between the pixel value of a pixel at the distal end of the subject with the line structure and the pixel values of pixels of smoothed images and the absolute values of the pixel value differences.

FIG. 14 is a diagram illustrating functions for acquiring synthesis weights according to a modified example of the first to third embodiments of the present invention.

FIG. 15 is a diagram illustrating functions for acquiring addition weights according to a modified example of the first to third embodiments of the present invention.

MODES FOR CARRYING OUT THE INVENTION

Embodiments embodying the present invention are hereinafter described on the basis of the drawings.

First Embodiment (Structure of Image Processing Apparatus)

The overall structure of an image processing apparatus 100 according to a first embodiment of the present invention is now described with reference to FIGS. 1 to 8. In the first embodiment, an example in which the image processing apparatus 100 is used for an X-ray imaging apparatus 101 is described. Note that the image processing apparatus 100 functions as an image processing apparatus according to the first embodiment of the present invention and also functions as a controller of the X-ray imaging apparatus 101. This is a measure for simplifying the apparatus structure, and the image processing apparatus 100 and the controller of the X-ray imaging apparatus 101 may be separate from each other and exchange data with each other.

Figure 1:
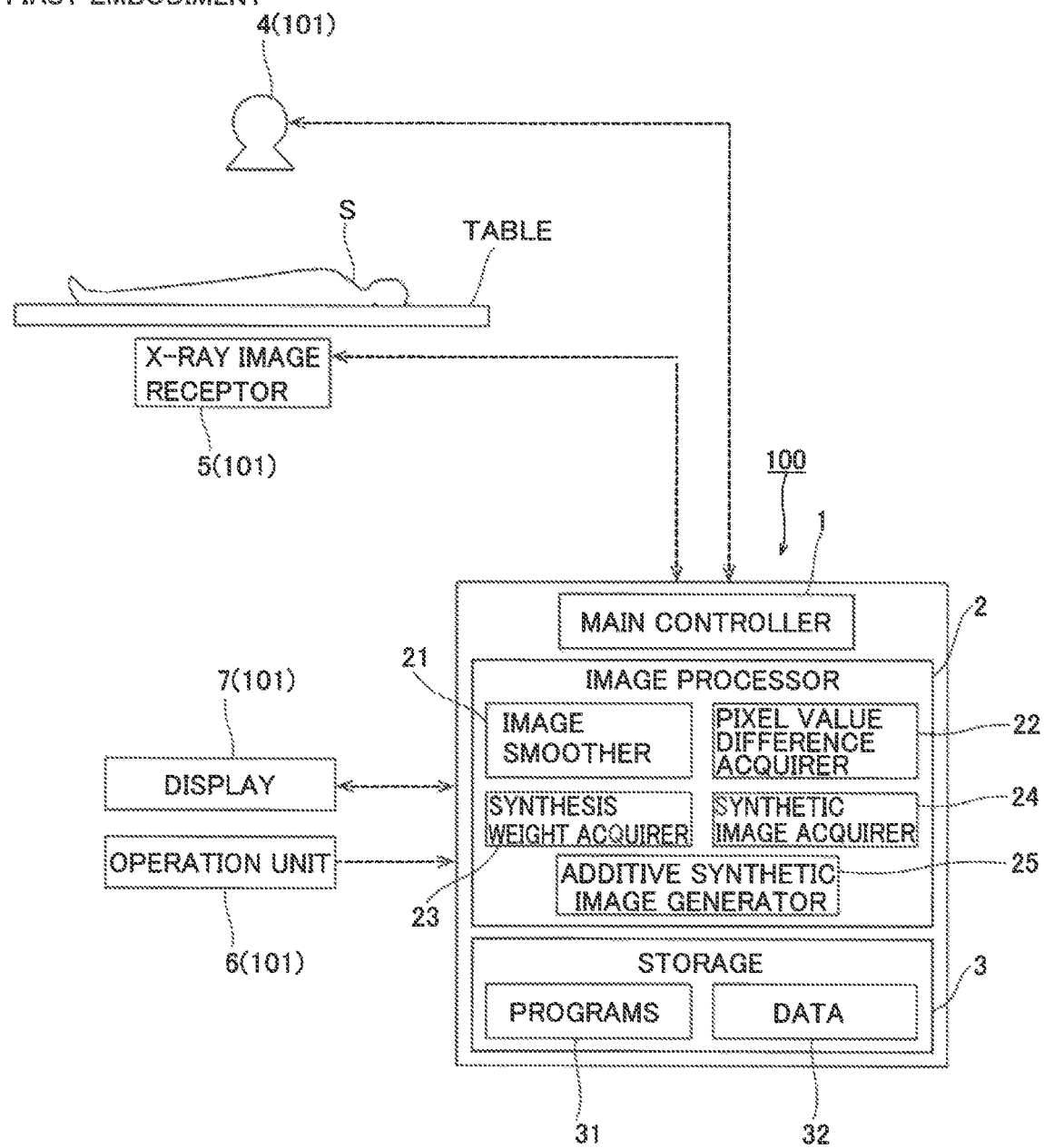
FIG. 1 is a block diagram showing an image processing apparatus according to a first embodiment of the present invention.

As shown in FIG. 1, the image processing apparatus 100 includes a main controller 1, an image processor 2, and a storage 3. The image processor 2 includes an image smoother 21, a pixel value difference acquirer 22, a synthesis weight acquirer 23, a synthetic image acquirer 24, and an additive synthetic image generator 25. The storage 3 includes programs 31 and data 32. Furthermore, the image processing apparatus 100 includes a PC (personal computer), for example, and functions as an image processing apparatus by appropriately retrieving the programs 31. The image processing apparatus 100 is connected to the X-ray imaging apparatus 101.

The main controller 1 executes the programs 31 stored in the storage 3 to cause the PC to function as the image processing apparatus 100 and to function as the controller of the X-ray imaging apparatus 101. The main controller 1 controls execution of X-ray imaging, the imaging direction, the imaging range, the number of times of imaging, etc. as a controller for the X-ray imaging apparatus 101. The function of the image processing apparatus 100 is described below.

The X-ray imaging apparatus 101 is connected to the image processing apparatus 100 that functions as the controller of the X-ray imaging apparatus 101, irradiates a subject S with X-rays to permit fluoroscopic viewing of a portion of the subject S to be image-captured (a portion to be subjected to fluoroscopy or a portion to be imaged) or image the portion of the subject S to be image-captured, and sends the captured image to the image processing apparatus 100. The X-ray imaging apparatus 101 includes an X-ray irradiator 4, an X-ray image receptor 5, an operation unit 6, and a display 7. Note that an X-ray image captured by the X-ray imaging apparatus 101 includes both an X-ray fluoroscopic image continuously captured with a low dose and an X-ray captured image captured with a high dose. The case in which X-ray imaging is performed is hereinafter described as a representative, but the same result is obtained for X-ray fluoroscopy.

The X-ray irradiator 4 irradiates the subject S with X-rays. The X-ray image receptor 5 receives the X-rays transmitted through the subject, converts data of the received X-ray captured image into an electrical signal, and sends the data of the X-ray captured image, which is an image In to be processed, to the image processing apparatus 100. The X-ray irradiator 4 and the X-ray image receptor 5 face each other via a table, and perform X-ray imaging on the subject S that lies on the table. The X-ray irradiator 4 includes an X-ray tube, for example. The X-ray image receptor 5 includes an FTP (Flat Panel Detector), for example.

The operation unit 6 receives an input of an operation command from an operator. Through the operation unit 6, the operator can perform an operation such as selection of an image processing method of the image processing apparatus 100 in addition to operating the X-ray imaging apparatus 101. The display 7 displays various screens associated with operations of the X-ray imaging apparatus 101 and the image processing apparatus 100 in addition to displaying the X-ray captured image processed by the image processing apparatus 100, for example. The operation unit 6 includes a keyboard, a mouse, an operation lever, etc. through which an operation input from the operator is received, for example. The display 7 includes a liquid crystal panel, a backlight, etc., for example.

(Image Smoothing Processing)

Image smoothing processing performed by the image processing apparatus 100 is now described with reference to FIGS. 2 to 6.

The image processing apparatus 100 acquires image data of a captured image (an X-ray fluoroscopic image or an X-ray captured image) with X-rays from the X-ray imaging apparatus 101. The case in which an X-ray captured image is acquired is considered below as a representative. The X-ray captured image is a grayscale image in which the magnitude of transmitted X-rays received for each pixel is expressed as a pixel value. In this case, only luminance is considered as a pixel value.

In the image processing apparatus, various types of image processing such as emphasis processing of the boundary of a subject included in an image, adjustment processing such as contrast, enlargement/reduction processing of an arbitrary portion, rotation processing, trimming processing, and positive-negative inversion processing, are performed on image data in order to improve the visibility of the image data for the operator, for example. The image processing apparatus 100 according to the first embodiment of the present invention performs the above image processing, significantly reduces or prevents variations due to noise components included in pixel values of pixels of an image, and performs smoothing processing to obtain an image excellent in visibility in which changes in the pixel values of the image are smooth. The image smoothing processing is described below in particular.

When noise components are included in the image, variations from ideal pixel values due to the noise components occur, and thus the image poor in visibility in which the pixel values do not change smoothly is obtained. These noise components occur for various reasons, but in the case of an X-ray captured image, for example, the X-ray irradiator 4 (X-ray tube) generates X-rays by causing thermal electrons to collide against an electrode such that non-uniformity (quantum noise which is statistical variation) of X-ray irradiation derived from Poisson distribution that cannot be avoided in principle is a major cause of noise components riding on the image. If the intensity of the X-rays radiated by the X-ray irradiator 4 is increased, the noise derived from the Poisson distribution can be reduced, but this is undesirable because the exposure doses of the subject S and the operator are increased at the same time. Therefore, it is necessary to remove the influence of the occurring noise components as much as possible even in a state in which the X-ray irradiation amount is kept low and to improve the visibility of the X-ray captured image. Note that the noise that occurs in the X-ray captured image includes noise that occurs when the X-ray image receptor 5 (FDP) retrieves the pixel values and noise that occurs in an electronic circuit due to extraneous electromagnetic waves, thermal noise, etc. during exchange of image data, for example. It should be noted that noise can be removed from a smoothed image acquired by the image processing apparatus 100 regardless of the cause of occurrence.

First, a smoothing method is briefly described. The image is locally substantially uniform as viewed in a sufficiently small range, and thus the pixel values are considered to be substantially equal in this range. That is, when it is assumed that each pixel is sufficiently fine, a pixel at a certain position of interest and a pixel at its peripheral position are considered to be substantially equal in pixel value. On the other hand, the noise components randomly ride on the respective pixel values, and thus the pixel values vary due to the noise components, and become larger values or smaller values than the original values. Therefore, the average value of the pixel values of the pixels at the position of interest and its peripheral position is acquired, and the pixel value of the pixel at the position of interest is replaced with the average value such that the noise components can be offset. Processing for replacement with the average value is performed on all the pixels such that a smoothed image with smoothed noise can be obtained.

If processing for taking average values with the pixel values of all the pixels at the peripheral positions is performed, the average values of the pixel values are taken while the boundaries are straddled when there are boundary portions in which the structure of the subject reflected in the image changes at the peripheral positions of the positions of interest. Thus, the boundary of the subject is also smoothed, and thus blurring occurs at the boundary of the subject. Therefore, it is necessary to emphasize smoothing in a direction along the structure of the subject and to perform smoothing so as to ignore smoothing in a direction across the boundary of the structure of the subject.

Figure 2:
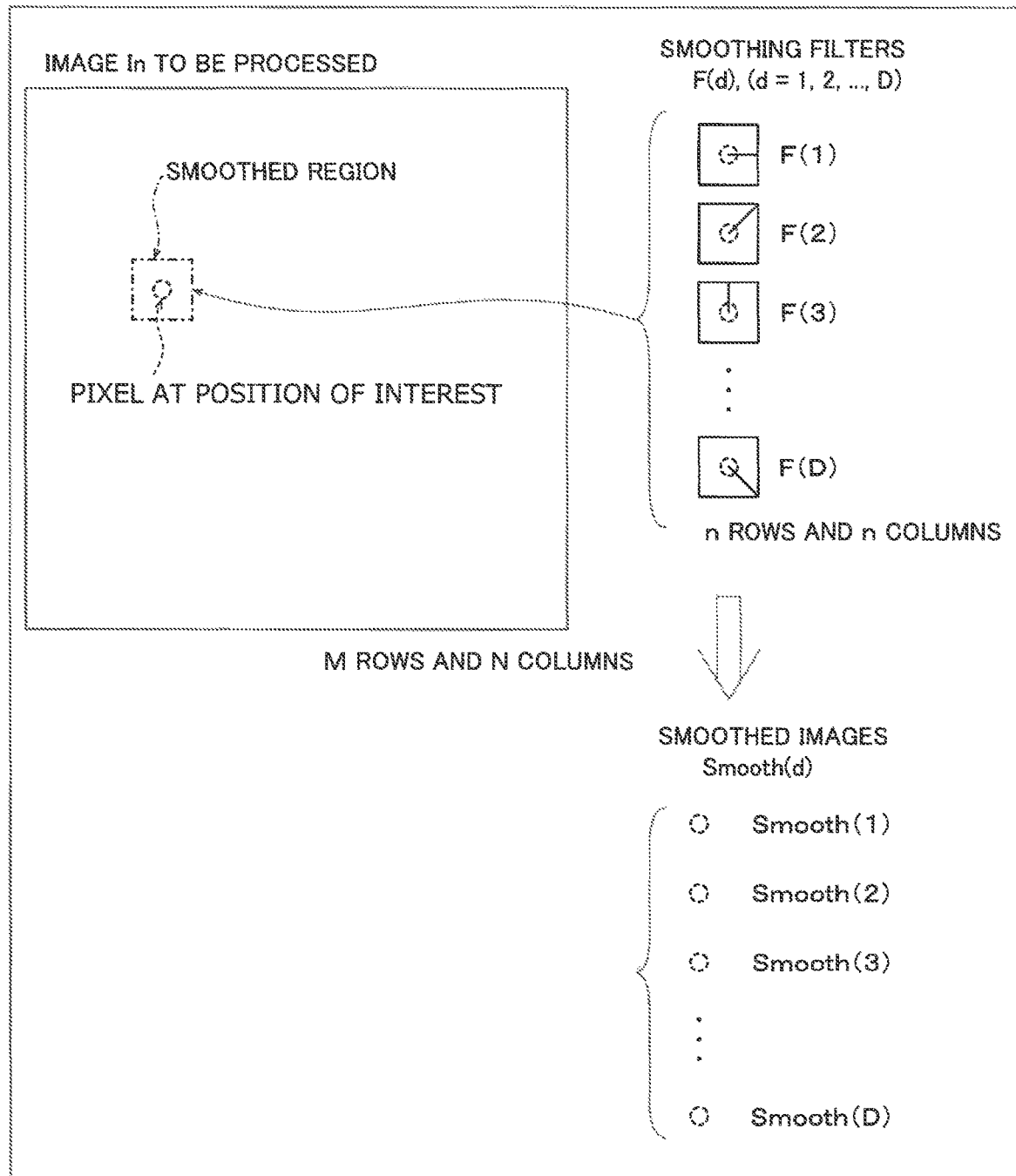
FIG. 2 is a diagram showing processing for acquiring smoothed images using smoothing filters for an image to be processed.

Specifically, as shown in FIG. 2, smoothing filters F(d) that perform smoothing in specific directions are prepared, for example, such that smoothing according to the structure of the subject is performed. The average value of the pixel values of pixels positioned on a line segment that extends in a specific direction centered on the pixel at the position of interest is taken, and processing for replacement as the pixel value at the position of interest is performed. Here, the image In to be processed is a collection of pixel data of M rows and N columns, and is an image to be smoothed. In addition, a portion surrounded by a dotted circle is the pixel at the position of interest, and a region surrounded by a square centered on the pixel at the position of interest is a smoothed region to be smoothed. There are D smoothing filters (d) according to directions in which smoothing is performed, and the smoothing filters (d) are anisotropic filters having different smoothing directions. Alphabet d is any positive integer value from 1 to D and a numerical value for distinguishing the smoothing filters F(d). Line segments shown in the smoothing filters F(d) indicate that pixels located on the line segments among the pixels at the position of interest and its peripheral position are pixels contributing to smoothing. The D smoothing filters F(d) are used for the image In to be processed to smooth the pixel values of the pixels at the position of interest and at the peripheral positions corresponding to the smoothing filters F(d) and acquire the pixel values of D smoothed images Smooth(d). The above smoothing processing using the D smoothing filters F(d) is performed on all the pixels of the image In to be processed, and the pixel values of D smoothed images Smooth(d) are obtained for each pixel.

Figure 3:
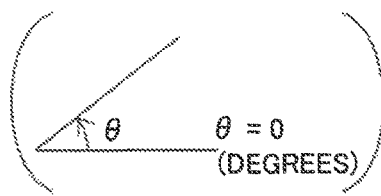
FIG. 3 is a diagram showing an example of smoothing filters of 5 rows and 5 columns that perform smoothing in line segment directions different from each other with a relationship of 45-degree intervals from a position of interest.

More specifically, the smoothing filters F(d) are expressed as matrices of operators having values as shown in FIG. 3, for example. In this case, the smoothing filters F(d) are expressed as eight matrices of 5 rows and 5 columns, and the pixel values of three adjacent pixels including the pixel at the position of interest are smoothed in eight directions at intervals of 45 degrees with the pixel value at the position of interest as the center. A coefficient ⅓ in the smoothing filters F(d) indicates that a pixel value at that position is acquired by multiplying the pixel value of the pixel of the image In to be processed at the corresponding position by ⅓ (coefficient multiplication). All the acquired pixel values are summed such that the average value of the pixel values of the pixels at the positions of the coefficient can be acquired. That is, with respect to the pixel at each position in the image In to be processed, the pixel values of the pixels of the eight smoothed images Smooth(d) can be obtained for each of the smoothing filters F(d). Note that blank spaces in which no coefficient is written are portions in which a coefficient of 0 is omitted, and indicate that pixels at the positions of the blank spaces do not contribute to smoothing. In addition, θ represents the direction of smoothing.

In order to obtain one synthetic image Comp from the eight smoothed images Smooth(d), weighted synthesis processing is performed to heavily weight and synthesize a smoothed image Smooth(d) on which smoothing is performed in the direction along the structure of the subject among the D smoothed images Smooth(d) and lightly weight and synthesize a smoothed image Smooth(d) on which smoothing is performed in the direction across the structure of the subject among the D smoothed images Smooth(d). Thus, the contribution of a smoothed image smoothed between pixels belonging to the same structure of the subject can be increased to perform synthesis, and the contribution of a smoothed image smoothed across portions having the different structures of the subject can be reduced to perform synthesis, and thus blurring of the boundary caused by smoothing across the boundary of the structure of the subject can be significantly reduced or prevented while the noise components are reduced by smoothing. Weighted synthesis of the smoothed images Smooth(d) is performed as described above for each pixel of the image In to be processed such that the synthetic image Comp, which is a result of appropriate smoothing, can be acquired.

As shown in FIG. 4, the number of smoothing filters F(d) can be further increased to set more smoothing directions. FIG. 4 is a diagram showing up to the third filter of twenty-four smoothing filters F(d) in which smoothing can be performed in twenty-four directions at intervals of 15 degrees. In this case, when smoothing is performed in a direction of 15 degrees or 30 degrees, it is necessary to perform smoothing in a direction across two pixels, and thus it is necessary to compensate for the contributions of the pixel values of the two straddled pixels in order to perform smoothing. For example, in a smoothing filter F (3) in which smoothing is performed in the direction of 30 degrees, coefficients k (1, 0) and coefficients k (1, 1) may be values obtained by distributing a coefficient of ⅓ corresponding to the contribution of one pixel value using tan(π/6), which is geometrically a tangent of 30 degrees. That is, k (1, 0) is tan(π/6)/3, and k (1, 1) is {1−tan(π/6)}/3. Actually, tan(π/6) is an irrational number, and thus the acquisition may be terminated with an appropriate number of digits according to the processing capacity of a calculator or the number of digits of a pixel value, and the result value may be stored in advance in the storage 3, retrieved from the storage 3 as appropriate, and used. Specific values of other coefficients are omitted. Furthermore, in the case of 45 degrees, the same structure as that of the smoothing filters shown in FIG. 3 is obtained. The smoothing filters F(d) after 45 degrees have the same structure as that obtained by rotating or inverting any of the above filters about the position of interest, and the illustration is omitted.

Although not shown, the sizes of the smoothing filters F(d) can be increased to n rows and n columns (7 rows and 7 columns, for example). In this case, similarly to the above, a coefficient obtained by equally dividing 1 may be distributed to pixels that exist in the smoothing direction, or a relatively large coefficient may be distributed to a pixel closer to the position of interest may be performed. In either case, in order to prevent pixel values of the entire image from changing before and after smoothing, it is necessary to perform normalization such that the total of coefficients included in each smoothing filter F(d) is 1.

Weighting of the smoothed images Smooth(d) is now specifically described. If the pixel value of the pixel of the image In to be processed and the pixel values of the pixels at the corresponding positions in the smoothed images Smooth(d) are close to each other, it can be considered that smoothing has been successfully performed between pixels belonging to a close portion of the structure of the subject having substantially the same pixel value. On the other hand, if the pixel value of the pixel of the image In to be processed and the pixel values of the pixels at the corresponding positions in the smoothed images Smooth(d) are largely different from each other, it can be considered that smoothing has been performed across the different structures of the subject (the boundary of the structure of the subject). Therefore, the pixel value of the pixel of the image In to be processed and the pixels value of the pixels of the smoothed images Smooth(d) are compared such that it can be determined which smoothed image Smooth(d) needs to be emphasized at the time of synthesis.

In such a case, the absolute values of differences between the pixel value of the pixel of the image In to be processed and the pixel values of the pixels of the smoothed images Smooth(d) are acquired, a smoothed image Smooth(d) having a small absolute value of the pixel value difference is more heavily weighted, and synthesis processing is performed.

Figure 5:
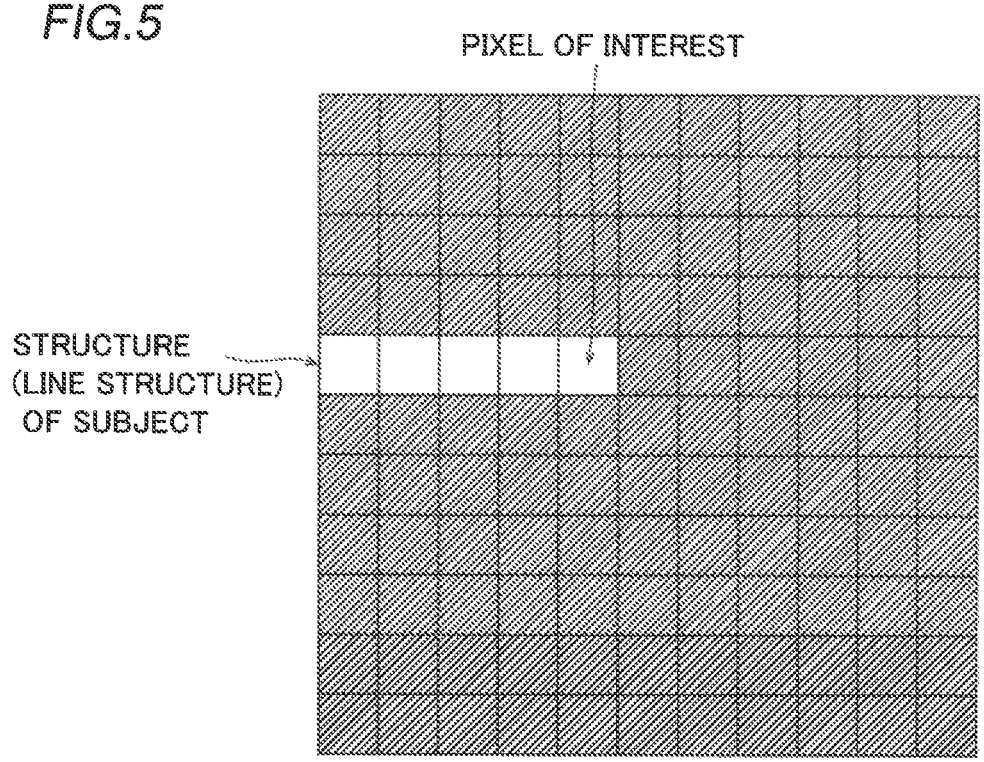
FIG. 5 is a diagram showing an example of an X-ray captured image in which a subject with a line structure is reflected.

Let us consider the case in which smoothing is performed on an image obtained by imaging a subject with a linear structure shown in FIG. 5. It is assumed that this subject S has a substantially uniform structure in the vicinity of a distal end. A portion shown in white is a portion in which reflection of the subject S is occurring, and the amount of X-rays that enter the X-ray image receptor 5 is reduced by the subject S. Thus, in the portion, the amount of X-ray reception is small. In addition, a portion shown by oblique lines is a portion in which reflection of the subject S is not occurring, and the X-rays radiated by the X-ray irradiator 4 enter the X-ray image receptor 5 without passing through the subject S. Thus, in the portion, the amount of X-ray reception is large.

At this time, twenty-four smoothing filters F(d) that smooth the pixel values of pixels on line segments that extend in twenty-four different directions at intervals of 15 degrees with the pixel at the position of interest as the center are used to acquire twenty-four smoothed images Smooth (d). Assuming that a distal end of the line structure is the position of interest, the pixel values of the pixels of the smoothed images Smooth(d) are subtracted from the pixel value of the pixel of the image In to be processed at the position of interest such that twenty-four pixel value differences S(d) corresponding to the smoothed images Smooth (d) are acquired.

A graph shown in FIG. 6(1) is a graph showing an ideal pixel value difference S(d) in which a positive and a negative have been taken into consideration in the case in which there is no noise component and the absolute value |S(d)| of the pixel value difference. The subject S becomes uniform at the distal end, and thus the pixel value difference S(d) becomes substantially zero in a direction of 180 degrees and becomes a more negative value as the direction deviates from 180 degrees. That is, in correspondence with the line structure of the subject S, the pixel value difference S(d) has a mountain-shaped graph with a peak close to 0 in the direction of 180 degrees. In this case, when the absolute value |S(d)| of the pixel value difference S(d) is taken, the absolute value |S(d)| has a valley-shaped graph with a peak close to 0 in the direction of 180 degrees due to positive-negative inversion. In this case, there is no influence of the noise components, and thus there is no difference in the direction obtained as a peak between the pixel value difference S(d) and the absolute value |S(d)| of the pixel value difference. That is, in cases of both the pixel value difference S(d) and the absolute value |S(d)| of the pixel value difference, a smoothed image Smooth(d) corresponding to the direction of 180 degrees, which is smoothed in a direction along the line structure, may be more heavily weighted to perform synthesis and acquire the synthetic image Comp.

Next, let us consider the case in which noise components ride on the pixel value of the pixel of the image In to be processed. The pixel value difference S(d) and the absolute value |S(d)| of the pixel value difference have graphs as shown in FIG. 6(2), for example, when there are the noise components. In this case, although the pixel value difference S(d) and the absolute value |S(d)| of the pixel value difference fluctuate in value due to the noise components, as an overall trend, the shapes in the graphs of FIG. 6(1) are substantially maintained. In other words, the pixel value difference S(d) has a mountain-shaped graph with a peak in the direction of 180 degrees, and the absolute value |S(d)| of the pixel value difference has a valley-shaped graph with a peak in the direction of 180 degrees.

On the other hand, a graph shown in FIG. 6(3) may be obtained depending on how the noise components ride. At this time, the pixel value difference S(d) corresponding to smoothing in the direction of 180 degrees should be substantially zero in a situation in which there is no noise component, but the pixel value difference S(d) deviates to a positive value due to superimposition of the noise components. Even in this case, the graph of the pixel value difference S(d) does not change as an overall trend, and thus the mountain-shaped graph is still maintained, and the peak of the graph is in the direction of 180 degrees. On the other hand, in the absolute value |S(d)| of the pixel value difference, a positive and a negative are not taken into consideration, and thus as shown in a right graph of FIG. 6(3), a peak is incorrectly considered to be in a direction corresponding to a smoothed image in a direction of 195 degrees. That is, weighted synthesis of the smoothed images Smooth(d) is performed with emphasis on the direction of 195 degrees. Such a misunderstanding of the direction of the structure occurs because a positive and a negative can be easily exchanged by the influence of the noise components when the pixel value difference S(d) is close to 0.

As described above, when smoothing is performed in consideration of the noise components, weighted synthesis of the smoothed images is performed based on the pixel value differences S(d) in which a positive and a negative have been taken into consideration instead of the absolute value |S(d)| of the pixel value difference such that weighted synthesis of the smoothed images Smooth(d) can be appropriately performed.

A series of processing for acquiring an additive synthetic image (processed image) Out, which is the final result of the smoothing processing, from the image In to be processed, using the pixel value differences S(d) in which a positive and a negative have been taken into consideration is described below in detail based on the structure of the image processing apparatus 100.

Here, the image processing apparatus 100 according to the first embodiment includes the image smoother 21 for acquiring the pixel values of respective pixels of a plurality of smoothed images Smooth(d) from a pixel value corresponding to the luminance or chromaticity of each pixel of the image In to be processed, using a plurality of smoothing filters F(d) different from each other and that smooth the noise components for each pixel of the image In to be processed.

Specifically, the image smoother 21 acquires the image In to be processed, which is an X-ray captured image acquired from the X-ray imaging apparatus 101. In this case, the image smoother 21 may store data of the X-ray captured image in the storage 3 and acquire the image In to be processed by retrieving the data from the storage 3 (data 32). In addition, the image smoother 21 acquires the pixel values of the pixels of a total number of D smoothed images Smooth(d) according to d for the pixel value of the pixel at each position in the image In to be processed, using the D smoothing filters F(d), which are matrices of operators including smoothing coefficients different from each other, for the image In to be processed. Calculation for acquiring the pixel value of the pixel corresponding to each position in the smoothed images Smooth(d) can be expressed as a mathematical formula (1).

[Mathematical Formula 1]

$$\text{Smooth}(d) = \text{In} \cdot F(d) \quad (1)$$

The operator shown by a black circle expresses calculation for acquiring the smoothed images Smooth(d) by acquiring the pixel value of the pixel at the position of interest in the image In to be processed and the pixel values of the pixels at the peripheral positions of the position of interest corresponding to the smoothing filters F(d), multiplying the acquired pixel values by the smoothing coefficients that differ from smoothing filter F(d) to smoothing filter F(d) and adding together to perform smoothing (arithmetic averaging, for example), and replacing the pixel value of the pixel at the position of interest by the obtained pixel value. Note that d is one of positive integer values corresponding to 1, 2, 3, . . . , D.

The image processing apparatus 100 according to the first embodiment further includes the pixel value difference acquirer 22 for acquiring the pixel value differences S(d) between the pixel value of each pixel of the image In to be processed and the pixel values of the respective pixels at the corresponding positions in the plurality of smoothed images Smooth(d), which are differences in the pixel values corresponding to the luminance or the chromaticity of each pixel, in which a positive and a negative have been taken into consideration, for each of the plurality of smoothing filters F(d).

Specifically, the pixel value difference acquirer 22 acquires the pixel value differences S(d), which are difference values in which a positive and a negative have been taken into consideration, between the pixel at each position in the image In to be processed and the pixels at the corresponding positions in the smoothed images Smooth(d). Calculation for acquiring the pixel value differences S(d) for each pixel can be expressed as a mathematical formula (2).

[Mathematical Formula 2]

$$S(d) = \text{In} - \text{Smooth}(d) \quad (2)$$

The image processing apparatus 100 according to the first embodiment further includes the synthesis weight acquirer 23 for acquiring synthesis weights α(d) used for weighting to combine the pixel values of the respective pixels of the plurality of smoothed images Smooth(d), based on the plurality of pixel value differences S(d).

Furthermore, the synthesis weight acquirer 23 according to the first embodiment acquires the average value AvrS of the plurality of pixel value differences S(d) in which a positive and a negative have been taken into consideration, and acquires a plurality of synthesis weights α(d) corresponding to each pixel based on the plurality of pixel value differences S(d) and the average value AvrS of the pixel value differences.

When it is defined that the pixel value differences increase from a negative toward a positive, the synthesis weight acquirer 23 according to the first embodiment is operable to perform control of increasing the synthesis weight α(d) of a smoothed image Smooth(d) corresponding to a smaller pixel value difference S(d) among the plurality of pixel value differences S(d) for each pixel when the average value AvrS of the pixel value differences is positive, and is operable to perform control of increasing the synthesis weight α(d) of a smoothed image Smooth(d) corresponding to a larger pixel value difference S(d) among the plurality of pixel value differences S(d) for each pixel when the average value AvrS of the pixel value differences is negative.

Specifically, the synthesis weight acquirer 23 arithmetically averages all the pixel value differences S(d) to acquire the average value AvrS of the pixel value differences. Calculation for acquiring the average value AvrS of the pixel value differences can be expressed as a mathematical formula (3).

[Mathematical Formula 3]

$$\text{Avr\_S} = \frac{\sum_{d=1}^{D} S(d)}{D} \quad (3)$$

The synthesis weight acquirer 23 acquires the synthesis weights α(d) of the smoothed images Smooth(d) based on the pixel value differences S(d) and the average value AvrS of the pixel value differences. The synthesis weights α(d) are positive real values, and normalization is made to bring the pixel values of the entire synthetic image Comp after synthesis to substantially the same level as the pixel values of the entire image In to be processed before synthesis and to make the sum of the number d of synthesis weights α(d) equal to exactly 1. Calculation for acquiring the synthesis weights α(d) can be expressed as a mathematical formula (4).

[Mathematical Formula 4]

$$\alpha(d) = k \times A(S(d), \text{AvrS}) \quad (4)$$

Here, k is a normalization constant for normalizing the synthesis weights α(d).

A function A is a function that takes the pixel value differences S(d) and the average value AvrS of the pixel value differences as arguments. As shown by the left graph of FIG. 6(3), when the pixel at the distal end of the line structure of the subject S is set as the position of interest, in the graph of the pixel value differences S(d) in which a positive and a negative have been taken into consideration, the pixel value difference S(d) corresponding to the smoothed image Smooth (d) along the direction of the structure has a convex peak. The pixel value of the pixel corresponding to a portion other than the line structure at the peripheral position of the position of interest in the image In to be processed is larger because relatively more X-rays are incident than at the position of interest. Thus, the pixel value differences S(d) corresponding to directions other than the direction along the line structure are negative values. Therefore, the average value AvrS of the pixel value differences is negative. Here, the peak of the graph of the pixel value differences S(d) corresponds to a pixel value difference S(d) farthest away in the positive direction among the pixel value differences S(d). That is, when it is defined that the pixel value differences increase from a negative toward a positive, the smoothed image Smooth(d) with a larger pixel value difference S(d) accommodates to smoothing along the direction of the structure when the average value AvrS of the pixel value differences is negative.

On the other hand, although not shown, let us consider a situation in which the position of interest is taken from a portion in which the subject S is not reflected and the boundary (structure) of the subject S is present at the peripheral position. In this case, blurring occurs at the edge of the image when smoothing is performed in the direction across the boundary of the subject S. Therefore, it is necessary to heavily weight and synthesize a smoothed image Smooth smoothed in a direction in which the subject S is not reflected. In addition, a pixel value difference S(d) corresponding to smoothing in the direction in which the subject is not reflected is substantially zero when there is no noise component. Furthermore, a pixel value difference S(d) corresponding to smoothing in the direction across the boundary of the subject is a positive value. In particular, a pixel value difference S(d) corresponding to smoothing in a direction perpendicular to the boundary of the subject is the largest value. Consequently, the graph of the pixel value differences S(d) in which a positive and a negative have been taken into consideration has a valley shape that protrudes downward and has a bottom (peak) at which S(d) corresponding to a smoothed image Smooth(d) smoothed perpendicular to the boundary of the subject S is close to 0. That is, the peak of the pixel value differences S(d) corresponds to a pixel value difference S(d) farthest away in the negative direction among the pixel value differences S(d), as described above. Furthermore, the pixel value differences S(d) corresponding to directions other than the direction in which the subject is not reflected are positive values, and thus the average value AvrS of the pixel value differences is positive. That is, when it is defined that the pixel value differences increase from a negative toward a positive, the smoothed image Smooth(d) with a smaller pixel value difference S(d) accommodates to smoothing along the direction of the structure when the average value AvrS of the pixel value differences is positive.

In summary, when it is defined that the pixel value differences increase from a negative toward a positive, the smoothed image Smooth(d) with a smaller pixel value difference S(d) accommodates to smoothing along the direction of the structure when the average value AvrS of the pixel value differences is positive, and the smoothed image Smooth(d) with a larger pixel value difference S(d) accommodates to smoothing along the direction of the structure when the average value AvrS of the pixel value differences is negative. That is, when the average value AvrS of the pixel value differences is positive, the function A may decrease the synthesis weight α(d) as the pixel value difference S(d) of the smoothed image Smooth(d) decreases, and when the average value AvrS of the value differences is negative, the function A may increase the synthesis weight α(d) as the pixel value difference S(d) of the smoothed image Smooth (d) increases. According to the first embodiment, when the average value AvrS of the pixel value differences is positive, the function A sets a synthesis weight α(dmin) corresponding to a smoothed image Smooth(dmin) having the smallest pixel value difference S(d) to 1, and sets the other synthesis weights α(d) to 0. Furthermore, when the average value AvrS of the pixel value differences is negative, the function A sets a synthesis weight α(d) corresponding to a smoothed image Smooth(dmax) having the largest pixel value difference S(d) to 1 and sets the other synthesis weights α(dmax) to 0. Note that dmin is d corresponding to the smallest S(d), and dmax is d corresponding to the largest S(d). When the function A is created as described above, only a smoothed image Smooth(d) corresponding to a direction in which the smoothing direction is optimum contributes to the synthetic image Comp.

When AvrS is 0, it is considered that there is no unique directionality in the pixel value of the pixel at the peripheral position of the position of interest. Therefore, when AvrS becomes 0, equal distribution to all synthesis weights α(d) is performed such that all synthesis weights α(d) may be 1/D, for example. In this case, the synthetic image Comp is an image evenly smoothed in all directions at the position of interest.

The image processing apparatus 100 according to the first embodiment further includes the synthetic image acquirer 24 that is operable to perform weighted synthesis on the respective pixels of the plurality of smoothed images based on the synthesis weights to acquire a synthetic image.

Specifically, the synthetic image acquirer 24 multiplies the smoothed images Smooth(d) by the synthesis weights α(d) acquired by the synthesis weight acquirer 23 and adds them to acquire a synthetic image Comp. Calculation for acquiring the synthetic image Comp can be expressed as a mathematical formula (5).

[Mathematical Formula 5]

$$Comp = \sum_{d=1}^{D} \{\alpha(d) \times Smooth(d)\} \quad (5)$$

In this case, the calculation of the mathematical formula (5) is the same as calculation for taking the smoothed image Smooth(dmin) corresponding to a direction in which the pixel value difference S(d) becomes the smallest as the synthetic image Comp when the average value AvrS of the pixel values is positive, and taking the smoothed image Smooth(dmax) corresponding to a direction in which the pixel value difference S(d) becomes the largest as the synthetic image Comp when the average value AvrS of the pixel values is negative.

The image processing apparatus 100 according to the first embodiment further includes the additive synthetic image generator 25 that is operable to perform weighted addition of the pixel value of each pixel of the image In to be processed and the pixel value of each pixel at the corresponding position in the synthetic image Comp for each pixel and is operable to perform synthesis to acquire an additive synthetic image Out.

Specifically, the additive synthetic image generator 25 weights the pixel value of each pixel of the image In to be processed, which is the original image, and the pixel value of each pixel at the corresponding position in the synthetic image, which is the result of smoothing, using an addition weight β and performs addition synthesis to acquire an additive synthetic image, which is the final result. The addition weight β is a positive real value between 0 and 1, and normalization is made to bring the pixel values of the entire additive synthetic image Out after addition synthesis to substantially the same level as the pixels values of the image In to be processed before synthesis and the pixel values of the entire synthetic image Comp. Calculation for acquiring the additive synthetic image Out with this addition weight β can be expressed as a mathematical formula (6).

[Mathematical Formula 6]

$$Out = (1-\beta) \times In + \beta \times Comp \quad (6)$$

Furthermore, the additive synthetic image generator 25 according to the first embodiment acquires the addition weight β corresponding to each pixel based on the pixel value of each pixel of the image In to be processed and the pixel value of each pixel at the corresponding position in the synthetic image Comp to acquire the additive synthetic image Out based on the addition weight β when performing weighted addition.

Specifically, the additive synthetic image generator 25 acquires the addition weight β for each pixel based on the pixel value of the image In to be processed and the pixel value at the corresponding position in the synthetic image Comp. Calculation for acquiring this addition weight β can be expressed as a mathematical formula (7).

[Mathematical Formula 7]

$$\beta = l \times B(In, Comp) \quad (7)$$

Note that l is a normalization constant for normalizing the addition weight β.

Here, a function B is a function that takes the pixel value of the image In to be processed and the pixel value of the synthetic image Comp as arguments. The function B is a function indicating the correlation between the image In to be processed and the synthetic image Comp, and increases as the pixel value of the image In to be processed and the pixel value of the synthetic image Comp are closer to each other. Thus, when the mathematical formula (6) and the mathematical formula (7) are combined, calculation for more heavily weighting and adding the pixel value of the synthetic image Comp as the pixel value of the image In to be processed and the pixel value of the synthetic image Comp become closer to each other, and more heavily weighting and adding the pixel value of the image In to be processed as the pixel value of the image In to be processed and the pixel value of the synthetic image Comp become farther from each other is obtained. That is, when the synthetic image Comp does not greatly change from the image In to be processed, it can be considered that the smoothing has worked well, and thus addition synthesis is performed with emphasis on the synthetic image Comp. On the other hand, when the synthetic image Comp greatly changes from the image In to be processed, it can be considered that distortion occurs due to a great change in pixel value due to smoothing, and thus addition synthesis is performed with emphasis on the image In to be processed.

Note that the function B that gives β can be defined as a function based on the absolute value |In −Comp| of a difference between the pixel value of each pixel of the image In to be processed and the pixel value of each pixel at the corresponding position in the synthetic image Comp, for example, as shown by a mathematical formula (8).

[Mathematical Formula 8]

$$B(In, Comp) = B(|In - Comp|) \quad (8)$$

Note that the function B relatively decreases in value when the absolute value |In −Comp|, which is an argument, increases.

As described above, the calculations from the mathematical formula (1) to the mathematical formula (8) are performed such that even when noise is present, smoothing can be appropriately performed according to the structure of the subject S, and the additive synthetic image Out in which blurring of the boundary (edge) of the subject S is significantly reduced or prevented can be acquired. Therefore, even when noise components occur in the pixel values of image data, the smoothed images are appropriately weighted such that image synthesis can be performed through appropriate smoothing.

A series of smoothing processing described above is described below with reference to flowcharts. Specific calculation for acquiring each image and value overlaps with the above description, and thus the specific calculation is properly omitted.

(Additive Synthetic Image Generation Processing)

Figure 7:
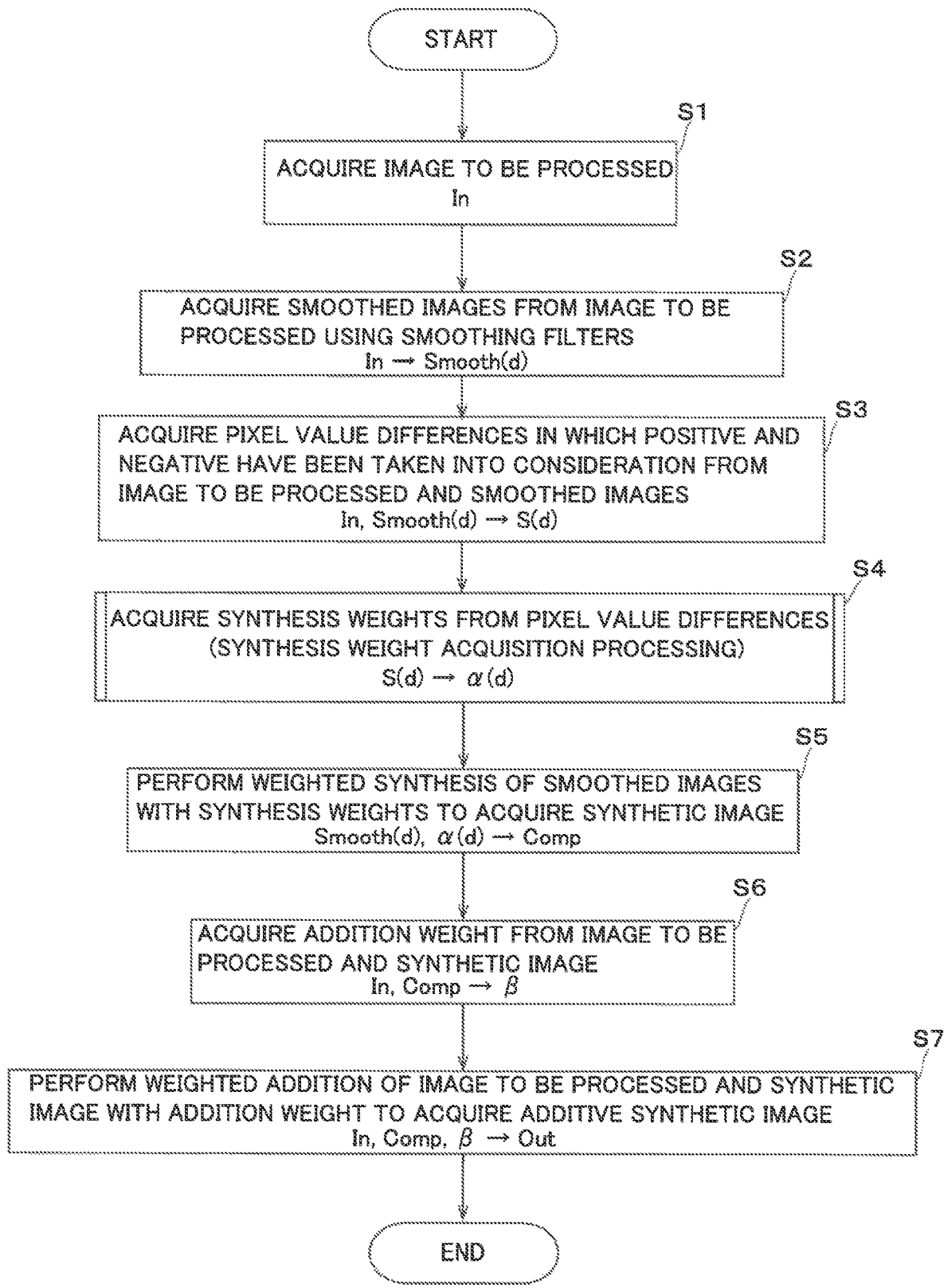
FIG. 7 is a flowchart illustrating additive synthetic image generation processing according to the first embodiment of the present invention.

A flow of additive synthetic image generation is now described with reference to a flowchart in FIG. 7.

First, when synthesis weight acquisition processing is started, the processing advances to step S1. In step S1, the image processor 2 acquires the image In to be processed (X-ray captured image), and the processing advances to step S2.

In step S2, the D smoothed images Smooth(d) are acquired using the D smoothing filters F(d) for the pixel value of each pixel included in the image In to be processed, and the processing advances to step S3.

In step S3, the difference values, in which a positive and a negative have been taken into consideration, between the pixel value of each pixel of the image In to be processed and the pixel values at the corresponding positions in the D smoothed images Smooth(d) are calculated for each d to acquire D pixel value differences S(d), and the processing advances to step S4.

In step S4, the synthesis weights α(d) corresponding to the pixel value differences S(d) are acquired, and the processing advances to step S5. A flow of the synthesis weight α(d) acquisition in step S4 is described separately below as the synthesis weight acquisition processing.

In step S5, weighted synthesis of the smoothed images Smooth(d) is performed with the synthesis weights α(d) such that the synthetic image Comp is acquired, and the processing advances to step S6.

In step S6, the addition weight β is acquired from the image In to be processed and the synthetic image Comp, and the processing advances to step S7.

In step S7, weighted addition of the image In to be processed and the synthetic image Comp is performed with the addition weight β such that the additive synthetic image Out is acquired, and the additive synthetic image generation processing is terminated.

The additive synthetic image generation processing described above is appropriately performed on each X-ray captured image acquired from the X-ray image receptor 5 or an external memory (not shown). Furthermore, the additive synthetic image Out acquired by the image processing apparatus 100 is stored in the storage 3, and can be appropriately retrieved and displayed on the display 7.

(Synthesis Weight Acquisition Processing)

Figure 8:
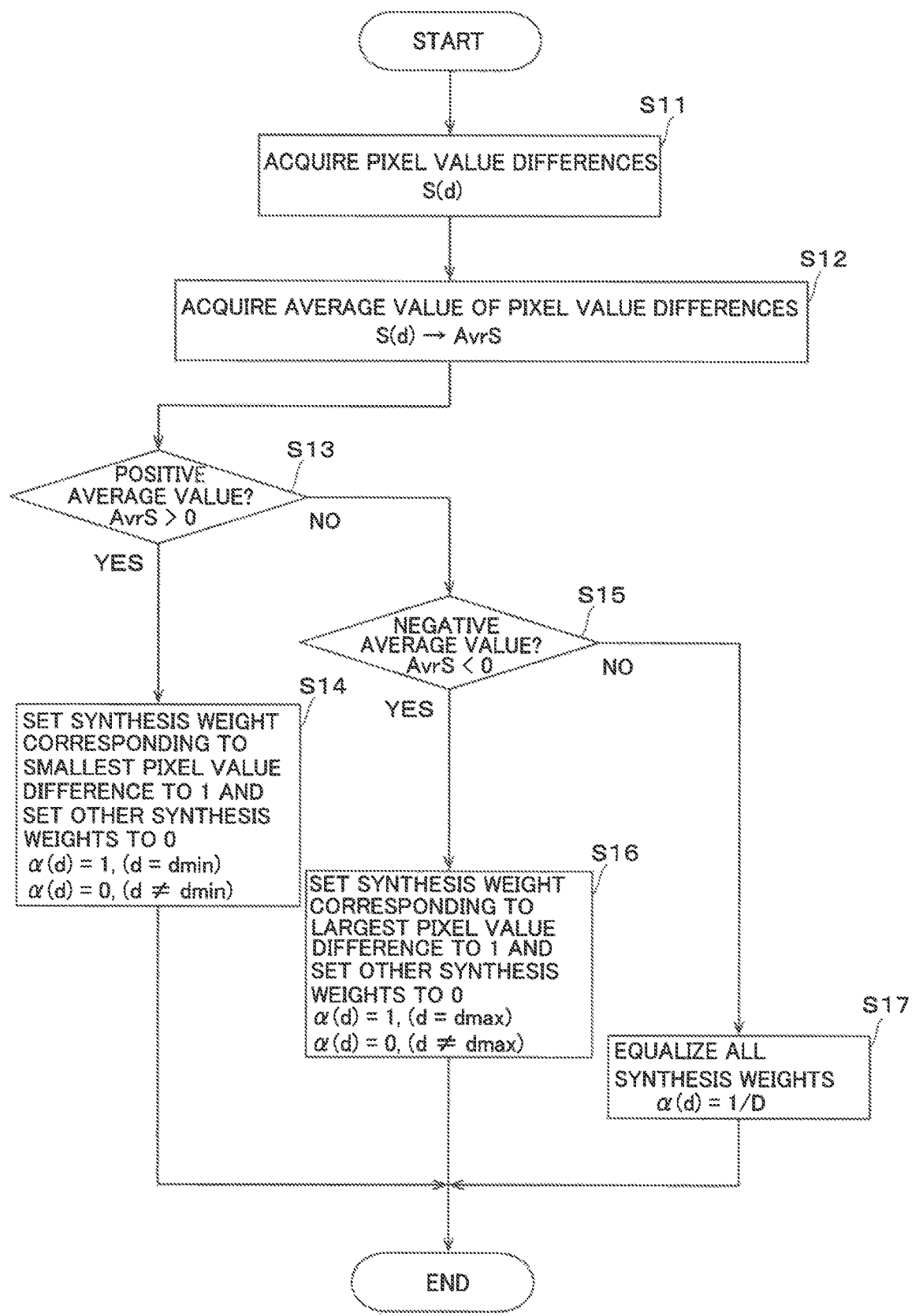
FIG. 8 is a flowchart illustrating synthesis weight acquisition processing according to the first embodiment of the present invention.

A flow of the synthesis weight acquisition processing is now described with reference to a flowchart in FIG. 8. This synthesis weight acquisition processing details the processing performed in step S4 of the additive synthetic image generation processing described above.

First, when the synthesis weight acquisition processing is started, the processing advances to step S11. In step S11, the image processor 2 (synthesis weight acquirer 23) acquires the pixel value differences S(d) in which a positive and a negative have been taken into consideration for each pixel, and the processing advances to step S12.

In step S12, the average value AvrS over all the pixel value differences S(d) is acquired, and the processing advances to step S13.

In step S13, it is determined whether or not the average value AvrS of the pixel value differences is a positive value. When it is a positive value, the processing advances to step S14, and when it is not a positive value, the processing advances to step S25.

In step S14, only the synthesis weight α(dmin) corresponding to an argument dmin that gives the smallest pixel value difference S(dmin) is set to 1, the synthesis weights α(d) corresponding to the other arguments d are set to 0, and the synthesis weight acquisition processing is terminated. When there are a plurality of arguments dmin that give the smallest pixel value difference S(dmin), the value of the synthesis weight α(dmin) may be a value obtained by dividing 1 by the number of arguments dmin. In this case, when there are two minimum pixel value differences S(dmin) with the same value, for example, the values of two synthesis weights α(dmin1) and α (dmin2) are set to 0.5(½).

In step S15, it is determined whether or not the average value AvrS of the pixel value differences is a negative value. When it is a negative value, the processing advances to step S16, and when it is not a negative value, the processing advances to step S17. When the processing advances to step S17, the average value AvrS of the pixel value differences is exactly 0.

In step S16, only the synthesis weight α(dmax) corresponding to an argument dmax that gives the largest pixel value difference S(dmax) is set to 1, the synthesis weights α(d) corresponding to the other arguments d are set to 0, and the synthesis weight acquisition processing is terminated. When there are a plurality of arguments dmax that give the largest pixel value difference S(dmax), the value of the synthesis weight α(dmax) may be a value obtained by dividing 1 by the number of arguments dmax. In this case, when there are two maximum pixel value differences S(dmin) with the same value, for example, the values of two synthesis weights α(dmin1) and α(dmin2) are set to 0.5(½).

In step S17, 1 is equally distributed to all the synthesis weights α(d), and the synthesis weight acquisition processing is terminated. When the total number of smoothing filters is D, the synthesis weight α(d) is 1/D.

As described above, in the synthesis weight acquisition processing, weighting (selection) can be easily performed with emphasis on the smoothed image Smooth(d) smoothed in an optimum direction based on the pixel value differences S(d) in which a positive and a negative have been taken into consideration and the average value AvrS of the pixel value differences.

Effects of First Embodiment

According to the first embodiment, the following effects are achieved.

According to the first embodiment, as described above, the synthesis weight acquirer 23 that is operable to perform weighted synthesis based on the plurality of pixel value differences S(d), in which a positive and a negative have been taken into consideration, between the pixel value of each pixel of the image In to be processed and the pixel values of the respective pixels at the corresponding positions in the plurality of smoothed images Smooth(d) to acquire the synthetic image Comp is provided. Accordingly, the overall trend of the pixel value differences S(d) in which a positive and a negative have been taken into consideration is considered to remain unchanged even when noise components occur, and thus unlike the case in which weighted synthesis of the smoothed images Smooth(d) is performed based on the absolute values |S(d)| of the pixel value differences S(d), the relationship of the pixel value differences S(d) is not reversed. Consequently, weighted synthesis of the smoothed images Smooth(d) can be appropriately performed based on the pixel value differences S(d) in which a positive and a negative have been taken into consideration. Specifically, when the pixel value differences S(d) are close to 0, the pixel value differences S(d) fluctuate across a positive and a negative near 0 due to the influence of the noise components, and thus when the absolute values |S(d)| of the pixel value differences S(d) are taken, a distinction cannot be made when the overall trend is considered. On the other hand, when the positive and the negative of the pixel value differences S(d) are stored, the overall trend of the pixel value differences S(d) does not greatly change even if noise components are present, and thus an appropriate smoothed image Smooth(d) can be selected to perform weighted synthesis. Thus, weighted synthesis of the smoothed images Smooth(d) can be appropriately performed, and an appropriately smoothed synthetic image Comp can be acquired.

According to the first embodiment, as described above, the synthesis weight acquirer 23 acquires the average value AvrS of the plurality of pixel value differences S(d) in which a positive and a negative have been taken into consideration and acquires the plurality of pixel value differences S(d) corresponding to each pixel based on the function A that takes the plurality of pixel value differences S(d) and the average value AvrS of the pixel value differences as arguments. Accordingly, a smoothed image having an unusual pixel value difference can be easily found based on the average value AvrS(d), which is the overall trend of the pixel value differences S(d), and thus weighted synthesis can be appropriately performed with the smoothed images Smooth(d) based on the pixel value differences S(d) in which a positive and a negative have been taken into consideration, indicating changes due to smoothing for each of the smoothing filters F(d).

According to the first embodiment, as described above, when it is defined that the pixel value differences increase from a negative toward a positive, the synthesis weight acquirer 23 is operable to perform control of increasing the synthesis weight α(d) of the smoothed image Smooth(d) corresponding to the smaller pixel value difference S(d) among the plurality of pixel value differences S(d) for each pixel when the average value AvrS of the pixel value differences is positive, and is operable to perform control of increasing the synthesis weight α(d) of the smoothed image Smooth(d) corresponding to the larger pixel value difference S(d) among the plurality of pixel value differences S(d) for each pixel when the average value AvrS of the pixel value differences is negative. Accordingly, when it is defined that the pixel value differences increase from a negative toward a positive, the smoothed image Smooth(d) having an unusual pixel value difference S(d) can be easily found based on the smaller pixel value difference S(d) apart from the overall trend toward a negative when the average value AvrS of the pixel value differences is positive. Furthermore, when it is defined that the pixel value differences increase from a negative toward a positive, the smoothed image Smooth(d) having an unusual pixel value difference S(d) can be easily found based on the larger pixel value difference S(d) apart from the overall trend toward a positive when the average value AvrS of the pixel value differences is negative. Therefore, the synthesis weight α(d) corresponding to the smoothed image Smooth(d) having an unusual pixel value difference S(d) can be easily increased based on the pixel value difference S(d) at the peak position (unique position) relative to the average value AvrS of the pixel value differences. Consequently, the synthetic image Comp obtained by more appropriately weighting the smoothed images Smooth (d) according to the overall trend of the pixel value differences S(d) and performing synthesis can be acquired.

According to the first embodiment, as described above, the additive synthetic image generator 25 that is operable to perform weighted addition of the pixel value of each pixel of the image In to be processed and the pixel value of each pixel at the corresponding position in the synthetic image Comp for each pixel and is operable to perform synthesis to acquire the additive synthetic image Out is provided. Accordingly, addition synthesis can be performed between the image In to be processed and the synthetic image Comp by further comparing the original image In to be processed and the synthetic image Comp, which is the result of smoothing, to consider the degree of change due to the smoothing.

According to the first embodiment, as described above, the additive synthetic image generator 25 acquires the addition weight β corresponding to each pixel based on the function B that takes the pixel value of each pixel of the image In to be processed and the pixel value of each pixel at the corresponding position in the synthetic image Comp as arguments and acquires the additive synthetic image Out based on the addition weight β when weighted addition is performed. Accordingly, the degree of weighting of addition of the image In to be processed and the synthetic image Comp can be easily acquired from the pixel value of each pixel of the image In to be processed and the pixel value of each pixel at the corresponding position in the synthetic image Comp.

Second Embodiment (Structure of Image Processing Apparatus)

Figure 9:
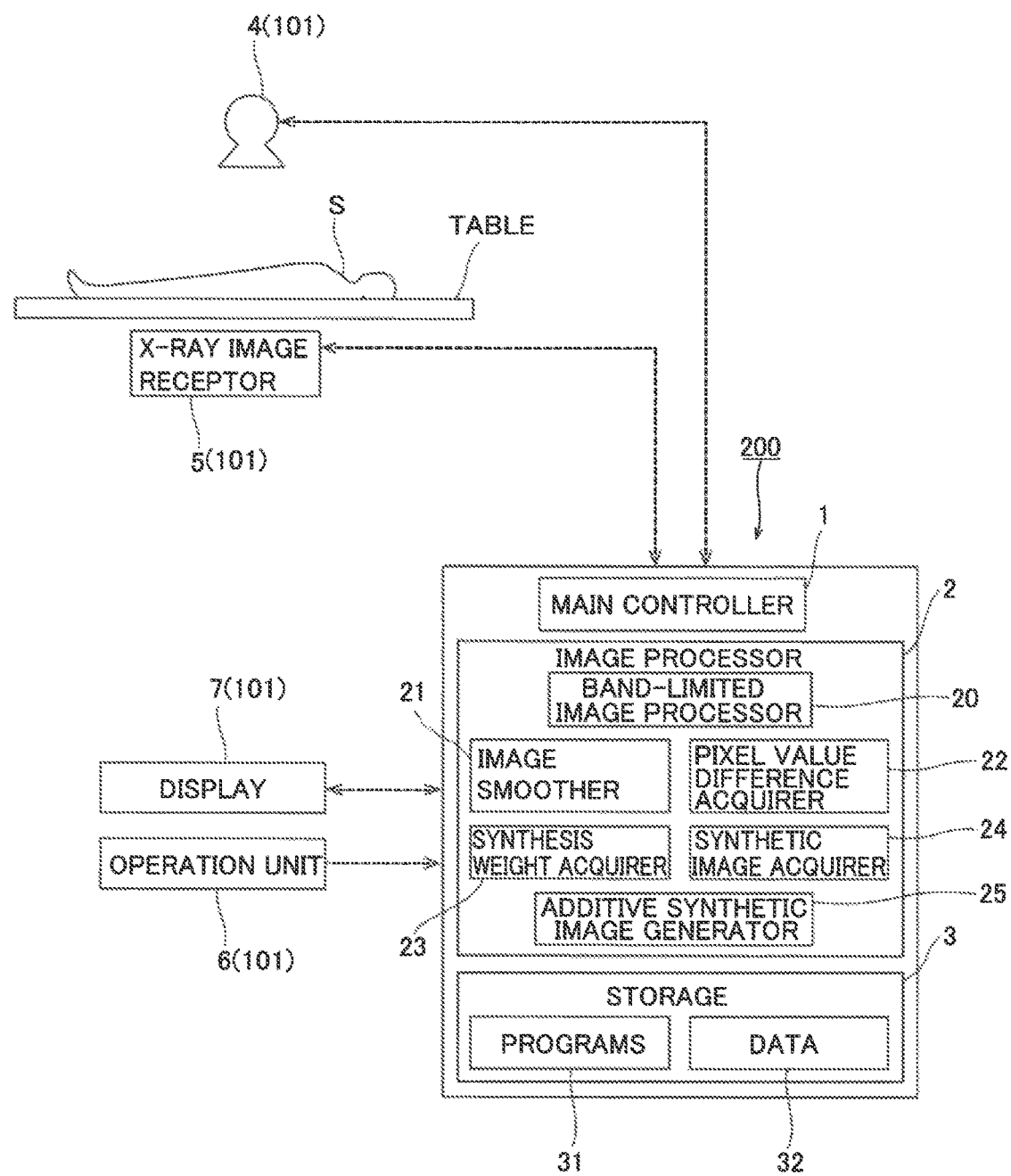
FIG. 9 is a block diagram showing an image processing apparatus according to a second embodiment of the present invention.

The overall structure of an image processing apparatus 200 according to a second embodiment of the present invention is now described with reference to FIGS. 9 to 12. In the second embodiment, as shown in FIG. 9, the structure including a band-limited image processor 20 that is operable to perform frequency analysis on an input image to acquire a plurality of images subjected to band limitation, in which only images containing specific frequencies are extracted, for respective frequencies and is operable to perform frequency synthesis to merge again the plurality of images divided for the respective frequencies, and for acquiring an output image on which the frequency synthesis has been performed, in addition to the structure of the first embodiment described above, is described. The same structures as those of the aforementioned first embodiment are denoted by the same reference numerals, and description thereof is omitted. Also in the second embodiment, an example in which the image processing apparatus 200 is used for an X-ray imaging apparatus 101 is described as in the first embodiment.

The image processing apparatus 200 according to the second embodiment further includes the band-limited image processor 20 that is operable to perform frequency analysis on an input image In1 to acquire a plurality of images subjected to band limitation, in which only images containing specific frequencies ωj are extracted, for respective frequencies ωj and is operable to perform frequency synthesis to recombine the plurality of images divided for the respective frequencies ωj, and for acquiring an output image on which the frequency synthesis has been performed, in addition to the structure of the first embodiment described above. In addition, the band-limited image processor is operable to perform frequency analysis on an image In to be processed as the input image In1 to acquire the image In to be processed, subjected to band limitation, acquires a synthetic image Comp subjected to band limitation and weighted synthesis based on pixel value differences S(d), in which a positive and a negative have been taken into consideration, for each pixel, is operable to perform frequency synthesis on images based on the synthetic image Comp subjected to band limitation and weighted synthesis, and acquires an output image Out1.

Figure 10:
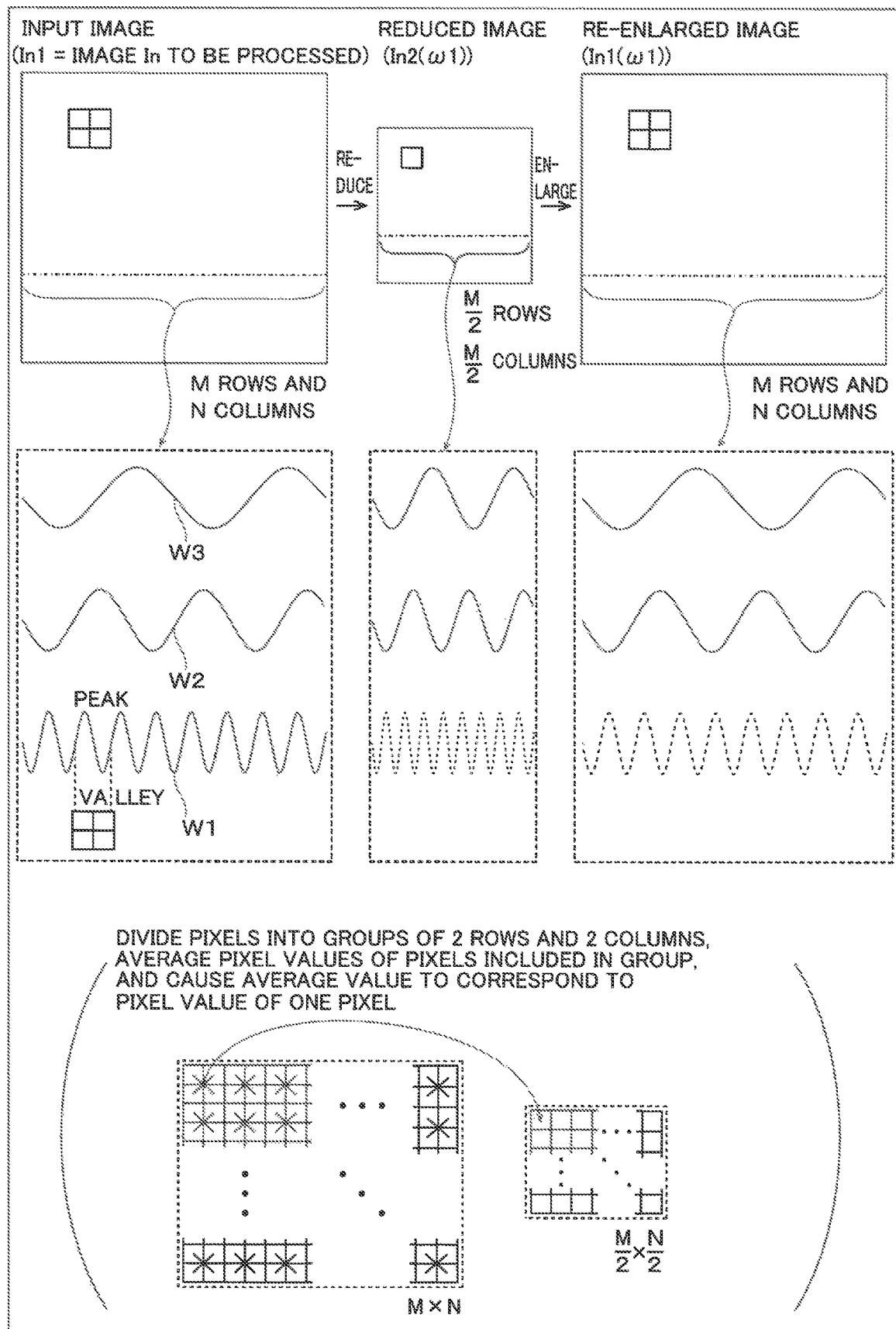
FIG. 10 is a diagram illustrating that a frequency component is removed by acquiring a reduced image with respect to an input image and re-enlarging the reduced image.
Figure 11:
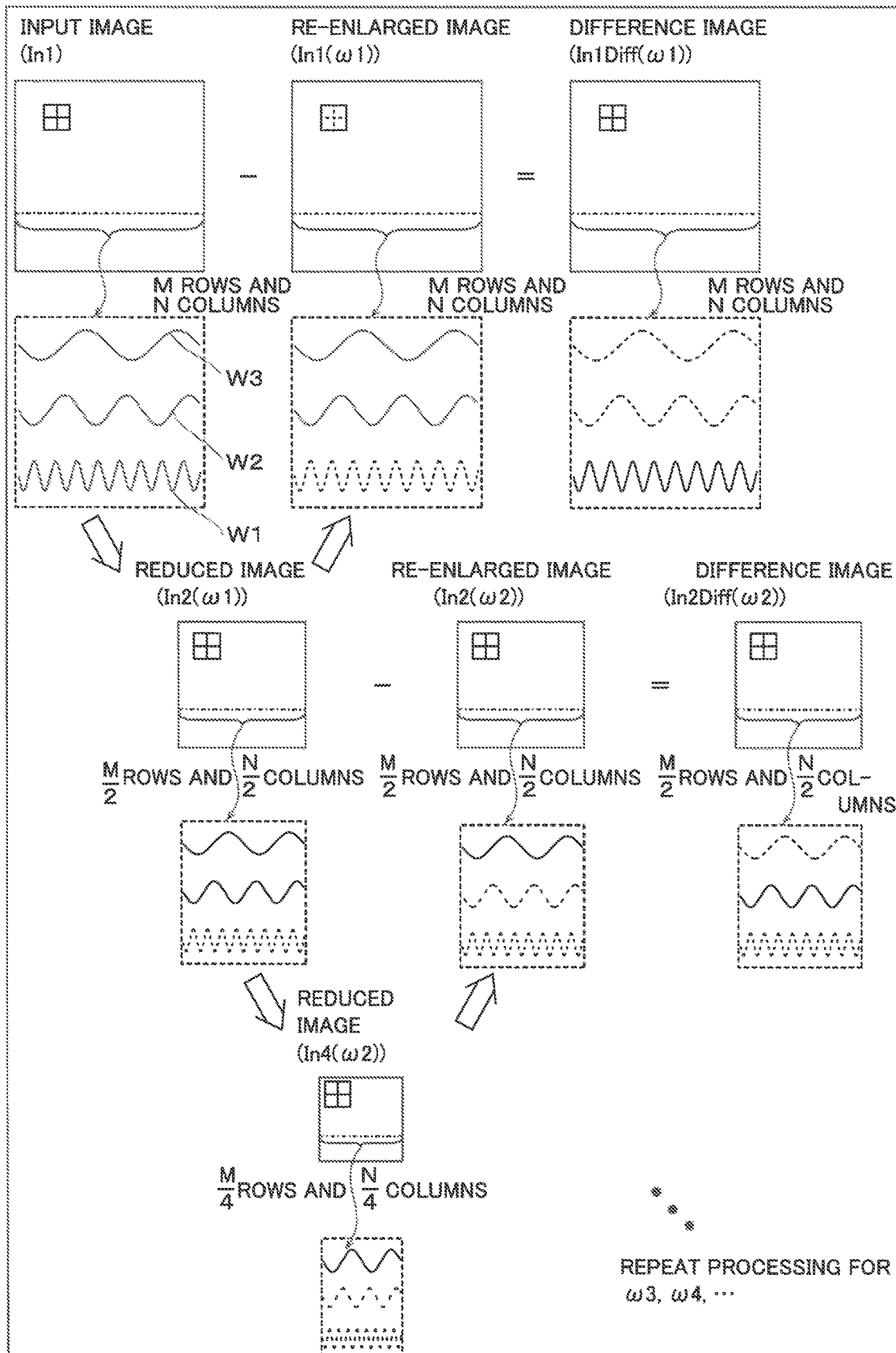
FIG. 11 is a diagram illustrating that only a specific frequency component remains by subtracting the pixel value of a pixel of a re-enlarged image from the pixel value of a pixel of the input image.

Specifically, as shown in FIGS. 10 and 11, the band-limited image processor 20 obtains a plurality of difference images IniDiff(ωj) subjected to band limitation from the input image In1. Here, i is an integer value corresponding to the power of 2, which is 1, 2, 4, . . . , and is a value indicating an image size as described below. In addition, the frequencies ωj correspond to the frequencies of pixel values included in the difference images IniDiff(ωj). First, as shown in parentheses at the bottom of FIG. 10, the band-limited image processor 20 divides pixels into groups of 2 rows and 2 columns enclosed by cross marks, causes a pixel value obtained by arithmetically averaging the pixel values of pixels in each of these groups (adding four pixel values and dividing the sum by four) to correspond to the pixel value of one pixel, and acquires a reduced image In2(ω1). Here, the input image In1 is a collection of pixels of M rows and N columns, and is the image In to be processed (X-ray captured image) itself. In addition, 1 in In1 indicates that the size of In1 is equal to (1×) the size of the original image In to be processed (X-ray captured image). Further, four pixels correspond to one pixel, and thus the vertical and horizontal widths of the reduced image In2(ω1) are ½ times, and the reduced image In2(ω1) is a collection of pixels of M/2 rows and N/2 columns.

Here, each pixel value included in an image has a certain pixel value, but an increase or decrease in pixel values taken out from pixels aligned in one row can always be expressed by adding a constant value to superimposition of many sine waves with different frequencies. For example, pixels on a line shown by a one-dot chain line shown in an image in FIG. 10 can be expressed by a group of several sine waves such as sine waves W1, W2, and W3 in a frame shown by a dotted line. In addition, the sine waves W1, W2, and W3 have frequency magnitudes of ω1, ω2, and ω3, respectively. The sine wave W1 has the highest frequency (shortest wavelength), the sine wave W2 has the second highest frequency, and the sine wave W3 has the lowest frequency. However, in the graphs of these sine waves, pixels and pixel values are sampled and quantized, and thus the graphs of these sine waves are microscopically represented by a collection of stepwise lines. The number of sine waves to represent pixel values is actually more than three. Furthermore, not only a horizontal row of pixel values but also a vertical row of pixel values can be expressed by superimposition of sine waves.

The component of a sine wave in which both a peak and a valley are contained in a matrix of 2 rows and 2 columns included in the input image In1 disappears by canceling between the peak and the valley in the process of averaging a group of pixels of 2 rows and 2 columns. Thus, as shown in FIG. 10, in the reduced image In2(ω1), the sine wave W1 having the highest frequency component disappears. In the reduced image In2(ω1), a corresponding sine wave of respective sine waves included in the input image In1 has a doubled frequency (half wavelength) in correspondence with the fact that the image widths halve.

The band-limited image processor 20 acquires a re-enlarged image In1(ω1) of M rows and N columns by causing one pixel of the reduced image In2(ω1) to correspond to four pixels. In the re-enlarged image In1(ω1), the pixel values of pixels belonging to each of groups partitioned into 2 rows and 2 columns are equal to each other, and are equal to the average of the pixel values of the pixels belonging to the same position in the original input image In1. In the re-enlarged image In1(ω1), the component of the sine wave W1 corresponding to the frequency ω1 disappears.

Next, as shown in FIG. 11, the band-limited image processor 20 subtracts the pixel value of the pixel at the corresponding position in the re-enlarged image In1(ω1) from the pixel value of the pixel of the input image In1 to acquire a difference image In1Diff(ω1). In the difference image In1Diff(ω1), only the component of the sine wave W1 corresponding to the frequency ω1 remains.

Furthermore, with respect to the reduced image In2(ω1) of M/2 rows and N/2 columns, pixels are enclosed by each group of 2 rows and 2 columns, the pixel values thereof are averaged, and the average is caused to correspond to one pixel such that a reduced image In4(ω2) of M/4 rows and N/4 columns is acquired. In this case, similarly to the above, the component of the sine wave W2 in which both a peak and a valley are contained in a matrix of 2 rows and 2 columns included in the reduced image In2(ω1) disappears by canceling between the peak and the valley. One pixel of the reduced image In4(ω2) is caused to correspond to four pixels such that a re-enlarged image In2(ω2) of M/2 rows and N/2 columns is acquired. A difference image In2Diff(ω2) is acquired by subtracting the pixel value of the pixel at the corresponding position in the re-enlarged image In2(ω2) from the pixel value of the pixel of the reduced image In2(ω1). In the difference image In2Diff(ω2), only the component of the sine wave W2 corresponding to the frequency ω2 remains. As described above, a positive value i attached to a reduced image Ini(ωj), for example, indicates that the vertical and horizontal widths of the image are $1/(2)^i$ times those of the input image In1. In the reduced image Ini(ωj), i matches $2^j$, and in a re-enlarged image Ini(ωj) and a difference image IniDiff(ωj), i matches $2^{(j-1)}$. Note that "a^b" represents calculation for raising a to an exponent b.

The above processing is repeated such that difference image IniDiff(ωj) having only a sine component corresponding to the frequency ω3, ω4, . . . can be acquired. Each time the processing is repeated, the horizontal and vertical size of the difference image IniDiff(ωj) is halved. Therefore, the band-limited image processor 20 acquires the difference image IniDiff(ωj) until an appropriate frequency ωj (the size of the corresponding image) at which the structure of a subject S can be read and aborts the processing for acquiring the difference image IniDiff(ωj). Furthermore, the sizes of all the obtained difference images IniDiff(ωj) and the size of the smallest reduced image Ini(ωj) used to obtain the smallest differential image IniDiff(ωj) are matched to the size of an image of M rows and N columns by repeatedly performing processing for appropriately causing one pixel to correspond to pixels of 2 rows and 2 columns and re-enlarging, and the pixel values of the pixels at the corresponding positions in the respective images are merged (added together) such that an image that matches with the original input image In1 can be acquired. That is, the processing for acquiring a plurality of difference images IniDiff(ωj) is equivalent to processing for acquiring the same by decomposing the input image In1 into a plurality of images, the frequency bands of which are limited to sine wave components corresponding to respective frequency ωj bands. The processing for acquiring the plurality of difference images IniDiff(ωj) in which the bands of the sine wave components are limited to the frequencies ωj from the input image In1 is an example of "processing for performing frequency analysis on the input image to acquire a plurality of images subjected to band limitation, in which only images containing specific frequencies are extracted, for respective frequencies" in the claims. The processing for matching the sizes of the difference images IniDiff(ωj) and merging is an example of "frequency synthesis processing for merging again a plurality of images divided for each frequency" in the claims.

The range occupied by the noise components, which ride on the pixel values of the image In to be processed (X-ray captured image), in the pixels has various sizes. Using a smoothing filter F(d) having a size matched to the size of a range occupied by noise components, for example, these noise components can be acquired by further weighting the pixel values of the smoothed image obtained for each size and performing image composition. Specifically, smoothing filters F(d) having a plurality of sizes such as a set of filters of 3 rows and 3 columns, a set of filters of 5 rows and 5 columns . . . , a set of filters of n rows and n columns may be prepared. However, although the size of the smoothing filter F(d) can be increased to an arbitrary size, the calculation amount becomes enormous as the size increases.

Here, the smoothing filter F(d) is used for the various difference images IniDiff(ωj) obtained by the above processing such that the size of the range occupied by the noise components also decreases in correspondence with a reduction in the image size because the difference image IniDiff(ωj) is a collection of images, the sizes of which decrease according to i. Furthermore, all the difference images IniDiff(ωj) can be merged again to return to the original input image In1. Thus, the smoothing filter F(d) having the same size is used for the difference images IniDiff(ωj) such that noise corresponding to the size of the smoothing filter F(d) can be removed, and thus the noise components that occupy a small range in the original input image In1 can be removed from a difference image IniDiff(ωj) having a large size, and the noise components that occupy a large range in the original input image In1 can be removed from a difference image IniDiff(ωj) having a small size. Thus, using D smoothing filters F(d) for each of the difference images IniDiff(ωj) acquired from the band-limited image processor 20, an image smoother 21 acquires D smoothed images Smooth(d) band-limited to a frequency of ωj for each frequency ωj band.

A pixel value difference acquirer 22 acquires D pixel value differences D(d) in which a positive and a negative have been taken into consideration based on the difference image IniDiff(ωj) as the image In to be processed and the D smoothed images Smooth(d) for each frequency ωj band. In addition, a synthesis weight acquirer 23 acquires D synthesis weights α(d) based on the pixel value differences S(d) and the average value AvrS of the pixel value differences for each frequency ωj band. In addition, a synthetic image acquirer 24 acquires a synthetic image Comp on which weighted synthesis has been performed based on the D smoothed images Smooth(d) and the D synthesis weights α(d) for each frequency ωj band. In addition, an additive synthetic image generator 25 acquires an additive synthetic image Out on which weighted addition and synthesis have been performed based on the difference image IniDiff(ωj) as the image In to be processed and the synthetic image Comp for each frequency ωj band. This additive synthetic image Out is an image in which the noise components for each frequency ωj band are removed from the difference image IniDiff(ωj) by smoothing, and has the same vertical and horizontal widths as those of the difference image IniDiff(ωj).

The band-limited image processor 20 matches the sizes of all the additive synthetic images Out acquired for each frequency ωj band with the size of the difference image IniDiff(ωj) having the smallest size, and acquires a merged output image Out1 from the pixel values of the corresponding pixels at each position. The processing for matching the image sizes is processing for repeating processing for doubling the vertical and horizontal widths of the image by replacing one pixel with a pixel having the same pixel value of 2 rows and 2 columns. The processing for acquiring the merged output image Out1 is processing for adding the pixel values of the pixels at the corresponding positions. The output image Out1 is smoothed for each sine wave component corresponding to each frequency band of the image In to be processed (input image In1), which is the original image, and is an image from which noise components with various sizes of the occupied ranges are appropriately removed.

Here, the image processing apparatus 200 according to the second embodiment acquires image data sent from the X-ray imaging apparatus 101 as the input image In1 (image In to be processed). In addition, as described above, the image processor 2 included in the image processing apparatus 300 acquires the difference image IniDiff(ωj) obtained by band-limiting the image In to be processed for each frequency ωj or the minimum reduced image Ini(ωj) as the image band-limited to the frequency ωj of the image In to be processed. Furthermore, the image processor 2 included in the image processing apparatus 300 performs additive synthetic image generation processing including synthesis weight acquisition processing on each acquired image band-limited to the frequency ωj and performs weighted synthesis of a plurality of smoothed images Smooth(d) acquired from each image based on the pixel value differences S(d) in which a positive and a negative have been taken into consideration to acquire the synthetic image Comp corresponding to the frequency ωj component, and performs addition synthesis of the image In to be processed, band-limited to the frequency ωj and the synthetic image Comp to acquire the additive synthetic image Out. Furthermore, the image processor 2 performs frequency synthesis by superimposing (adding) the additive synthetic image Out band-limited to the frequency ωj over all ωj, and acquires the merged output image Out1.

(Band-by-Band Additive Synthetic Image Generation/Merging Processing)

Figure 12:
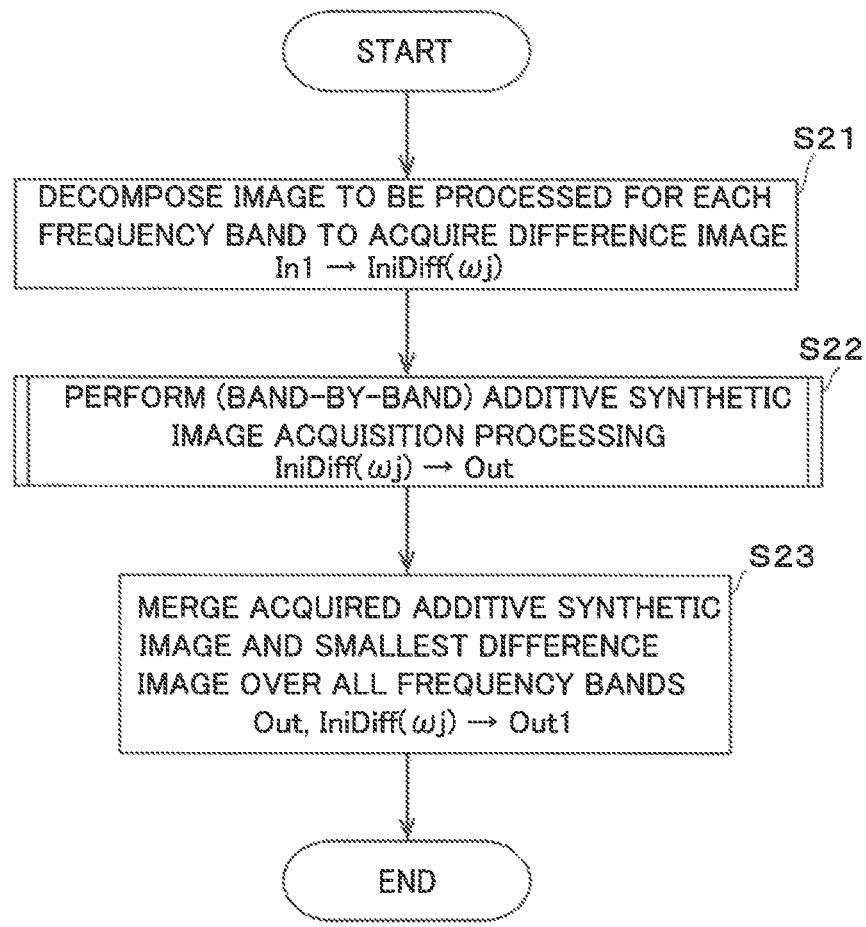
FIG. 12 is a flowchart illustrating band-by-band additive synthetic image generation/acquisition processing according to the second embodiment of the present invention.

A flow of band-by-band additive synthetic image generation/merging processing is now described using a flowchart with reference to FIG. 12.

First, when the band-By-band additive synthetic image generation/merging processing is started, the processing advances to step S21. In step S21, frequency analysis is performed on the input image Int, which is the image In to be processed, and the difference image IniDiff($\omega$j) including only a frequency component corresponding to the predetermined frequency $\omega$j band in the pixel value is acquired for each $\omega$j, and the processing advances to step S22.

In step S22, the additive synthetic image generation processing is performed on the difference image IniDiff($\omega$j) including only the frequency component corresponding to the frequency $\omega$j band in the pixel value, and the additive synthetic image Out including only the frequency component of the band corresponding to the frequency $\omega$j as pixel values is acquired, and the processing advances to step S23. The noise components are smoothed for each difference image IniDiff($\omega$j) in the process of performing the additive synthetic image generation processing, and thus the noise components can be removed for each frequency $\omega$j band. Note that the additive synthetic image generation processing and the synthesis weight acquisition processing executed during the additive synthetic image generation processing according to the second embodiment are equivalent to the additive synthetic image generation processing and the synthesis weight acquisition processing executed during the additive synthetic image generation processing according to the first embodiment.

In step S23, the size of the acquired additive synthetic image Out and the size of the difference image IniDiff($\omega$j) having the smallest size are matched, and synthesis is performed over all the frequency $\omega$j bands such that the merged additive synthetic image is acquired, and the band-by-band additive synthetic image generation/merging processing is terminated.

In the second embodiment, the same reference numerals are used for the structures common to those of the aforementioned first embodiment, and description thereof is omitted.

(Effects of Second Embodiment)

According to the second embodiment, the following effects are achieved.

According to the second embodiment, similarly to the first embodiment, the synthesis weight acquirer 23 that performs weighted synthesis based on the plurality of pixel value differences S(d), in which a positive and a negative have been taken into consideration, between the pixel value of each pixel of the image In to be processed and the pixel values of the respective pixels at the corresponding positions in the plurality of smoothed images Smooth(d) acquired for the image In to be processed to acquire the synthetic image Comp is provided. Accordingly, weighted synthesis of the smoothed images Smooth(d) can be appropriately performed to acquire an appropriately smoothed synthetic image Comp.

According to the second embodiment, as described above, the band-limited image processor 20 that is operable to perform frequency analysis on the input image In1, which is the image In to be processed, to acquire the plurality of difference images IniDiff($\omega$j) subjected to band limitation, in which only difference images IniDiff($\omega$j) containing specific frequencies $\omega$j are extracted, for respective frequencies $\omega$j is operable to perform frequency synthesis to merge again the plurality of difference images IniDiff($\omega$j) divided for the respective frequencies, and for acquiring the output image Out1 on which the frequency synthesis has been performed is provided. Accordingly, the plurality of smoothed images Smooth(d) are acquired for each sine wave component corresponding to the frequency $\omega$j included in the image In to be processed, weighted synthesis of the pixel values of the pixels at the corresponding positions in the plurality of smoothed images Smooth(d) is performed based on the plurality of pixel value differences S(d) in which a positive and a negative have been taken into consideration, and the synthetic image Comp is acquired such that the noise components can be smoothed for each frequency $\omega$j band. Consequently, weighted synthesis of the smoothed images Smooth(d) for each frequency $\omega$j in which the noise components are smoothed can be more effectively performed while blurring of the boundary of the structure of the subject S reflected on the image In to be processed is significantly reduced or prevented. Furthermore, the additive synthetic image Out obtained by performing addition synthesis of the obtained synthetic image Comp and the image In to be processed is merged over all the frequencies $\omega$j such that the output image Out1, which is an image appropriately smoothed for each frequency $\omega$j, can be acquired from the original image In to be processed.

The remaining effects of the second embodiment are similar to those of the aforementioned first embodiment.

Third Embodiment

Figure 13:
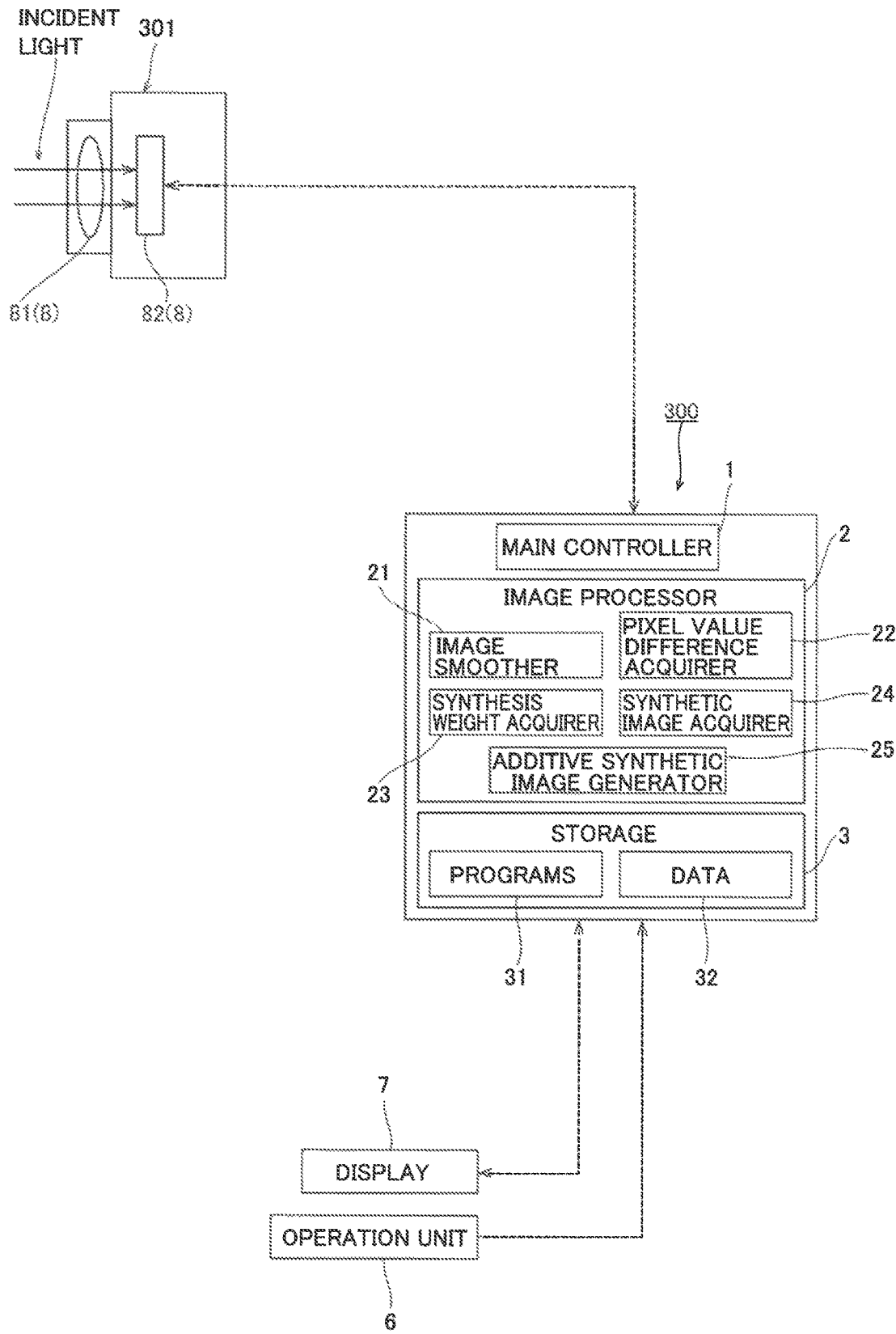
FIG. 13 is a block diagram showing an image processing apparatus according to a third embodiment of the present invention.

The overall structure of an image processing apparatus 300 according to a third embodiment of the present invention is now described with reference to FIG. 13. In the third embodiment, as shown in FIG. 13, the image processing apparatus 300 is used for a low-light camera 301 unlike the aforementioned first embodiment. The same structures as those of the aforementioned first embodiment are denoted by the same reference numerals, and description thereof is omitted.

In the third embodiment, the image processing apparatus 300 is connected to the low-light camera 301 including an imager 8 including an imaging optical system 81 and an imaging device 82. Furthermore, the image processing apparatus 300 is connected to an operation unit 6 and a display 7.

The imaging optical system 81 optically adjusts incident light from the outside and sends it as incident light to the imaging device 82. The imaging device 82 converts amplified light into an electrical signal, and sends it as image data to the image processing apparatus 300. The imaging optical system 81 includes one lens or a combination of a plurality of lenses. Furthermore, the imaging device 82 includes a CCD (Charge Coupled Device) image sensor or a CMOS (Complementary Metal Oxide Semiconductor) image sensor, for example. Note that the imaging device 82 may be a cooled CCD image sensor or a cooled CMOS image sensor.

In imaging with the low-light camera 301, a high-resolution image is acquired in a state in which the amount of light is small, and thus noise components are likely to occur in the pixel value of a pixel. Therefore, even when noise components ride on the pixel value, it is necessary to perform smoothing appropriately. Note that the low-light camera 301 can acquire not only the light amount of incident light but also the wavelength, and unlike the case of the X-ray imaging apparatus 101, the pixel value of the pixel of an image includes luminance and chromaticity. Chromaticity can also be smoothed by the same processing as that for luminance, and thus noise components can be reduced by individually performing smoothing processing on luminance and chromaticity.

The image processing apparatus 300 according to the third embodiment acquires the image data sent from the low-light camera 301 as an image In to be processed. An image processor 2 included in the image processing apparatus 300 performs additive synthetic image generation processing including synthesis weight acquisition processing on the acquired image In to be processed and performs weighted synthesis on a plurality of smoothed images Smooth(d) acquired from the image In to be processed based on pixel value differences S(d) in which a positive and a negative have been taken into consideration to acquire a synthetic image Comp, and performs addition synthesis of the image In to be processed and the synthetic image Comp to acquire an additive synthetic image Out.

Effects of Third Embodiment

According to the third embodiment, the following effects are achieved.

According to the third embodiment, similarly to the first embodiment, a synthesis weight acquirer 23 that performs weighted synthesis based on the plurality of pixel value differences S(d), in which a positive and a negative have been taken into consideration, between the pixel value of each pixel of the image In to be processed and the pixel values of the respective pixels at the corresponding positions in the plurality of smoothed images Smooth(d) to acquire the synthetic image Comp is provided. Accordingly, even when the noise components occur in the pixel value of the pixel of the image In to be processed captured by the low-light camera 301, weighting is appropriately performed on the smoothed images Smooth(d) acquired from the image In to be processed such that image synthesis can be performed through appropriate smoothing.

The remaining structures and effects of the third embodiment are similar to those of the aforementioned first embodiment.

Modified Examples

The embodiments disclosed this time must be considered as illustrative in all points and not restrictive. The scope of the present invention is not shown by the above description of the embodiment but by the scope of claims for patent, and all modifications (modified examples) within the meaning and scope equivalent to the scope of claims for patent are further included.

For example, while the example in which the image processor 2 individually executes the calculations represented by the mathematical formulas (1) to (8) to acquire the additive synthetic image Out has been shown in each of the aforementioned first to third embodiments, the present invention is not restricted to this. According to the present invention, the image processor 2 may combine a plurality of mathematical formulas into one to execute a calculation. For example, an additive synthetic image may be acquired by executing a calculation represented by the following mathematical formula (9) into which the mathematical formulas (5) and (6) have been combined. In this case, step S5 and step S7 of the additive synthetic image generation processing are combined into one step, and acquisition of the synthetic image Comp is omitted.

[Mathematical Formula 9]

$$\text{Out} = (1-\beta) \times \text{In} + \beta \times \sum_{d=1}^{D} \{\alpha(d) \times \text{Smooth}(d)\} \quad (9)$$

Incidentally, in the case of the above mathematical formula (9), β is changed so as to be acquired from the function B that takes the image In to be processed and the smoothed images Smooth(d) as arguments.

The image processor 2 may acquire the calculation results of the mathematical formulas (1) to (8) by retrieving the same from data stored in the storage 3 as results of calculations executed in advance. That is, calculation processing may be appropriately replaced with reference processing using an LUT (Lookup Table), for example.

While the example in which the image processor 2 performs weighting and addition synthesis of the image In to be processed and the synthetic image Comp to acquire the additive synthetic image Out has been shown in each of the aforementioned first to third embodiments, the present invention is not restricted to this. According to the present invention, the image processor 2 may directly acquire the synthetic image Comp as a processed image on the assumption that smoothing of the image In to be processed is achieved at the time of acquiring the synthetic image Comp.

While the synthesis weight α(d) corresponding to the smoothed image Smooth in which the direction of smoothing is conceivably the most appropriate is set to 1, and the synthesis weights α(d) corresponding to the smoothed images Smooth in the other directions are set to 0 in each of the aforementioned first to third embodiments, the present invention is not restricted to this. According to the present invention, a value may be distributed to a plurality of synthesis weights α(d) such that the sum becomes 1. Specifically, for example, when the average value AvrS of the pixel value differences is negative, the synthesis weight corresponding to the smoothed image Smooth(d) in which the pixel value difference S(d) becomes the largest may be set to ⅔, and the synthesis weight corresponding to the smoothed image Smooth(d) in which the pixel value difference S(d) becomes the second largest may be set to ⅓.

As another configuration for acquiring the synthesis weight α(d), the pixel value difference S(d) and the function A (S(d), AvrS) that gives the synthesis weight α(d) can be associated with each other by functions shown in FIG. 14. The functions in FIG. 14 correspond to the case in which the average AvrS of the pixel value differences is negative. When the average AvrS of the pixel value differences is negative, it is considered that smoothing is performed in a direction closer to the peak close to 0, in which smoothing has worked well, as the pixel value difference S(d) becomes a larger value in the positive direction. Therefore, it is necessary to increase the value of the synthesis weight α(d) corresponding to the smoothed image with a larger pixel value difference S(d) in the positive direction.

Assuming that the normalization constant k applied to the function A in the formula (4) is a positive real value, the shape of the function of α(d) and the shape of the function A can be almost equated, and thus the function A is described below. The function A shown in FIG. 14(1) is a step function, which is a function that switches from 0 to a positive constant value with a certain threshold as the pixel value difference S(d) increases. This step function is used such that the synthesis weight α(d) can become a positive value only when the pixel value difference S(d) becomes equal to or higher than the certain threshold, and the synthesis weight α(d) can become zero when the pixel value difference S(d) is less than the certain threshold.

The function A shown in FIG. 14(2) is a linear function, which is a function that smoothly increases (is proportional) with a constant increase rate as the pixel value difference S(d) increases. This linear function is used such that α(d) can smoothly increase as the pixel value difference S(d) increases.

The function A shown in FIG. 14(3) is a logistic function having an inflection point, which is a function that asymptotically approaches 0 when the pixel value difference S(d) is small and sufficiently far from the position of the inflection point toward the negative value side (left side), increases such that its increase rate increases as the pixel value difference S(d) increases, has an increase rate maximized at the position of the inflection point (threshold) and turned to decrease, and asymptotically approaches a positive constant value when the pixel value difference S(d) is large and sufficiently far from the position of the inflection point toward the positive value side (right side). This logistic function has a property intermediate between the step function and the linear function. That is, at a position sufficiently far from the inflection point (threshold), the synthesis weights α(d) are distributed to a certain positive constant value and zero as in the step function, and at a position close to the inflection point, α(d) is smoothly increased or decreased.

Therefore, by using this logistic function, when the pixel value difference S (d) is sufficiently large, the synthesis weight α (d) becomes a positive value, and when the pixel value difference S (d) is sufficiently small, The weight α (d) becomes 0, and when the pixel value difference S (d) is an intermediate value, the synthesis weight α (d) changes smoothly. Unlike the step function, the logistic function does not rapidly change the synthesis weight α(d) depending on whether or not the pixel value difference S(d) exceeds the threshold, and thus weighted synthesis can be smoothly performed. In addition, unlike the linear function in which weighting is performed in proportion to the pixel value difference S(d), the logistic function heavily weights the synthesis weight α(d) corresponding to the smoothed image with a sufficiently large pixel value difference S(d) and sets the synthesis weight α(d) corresponding to the smoothed image with a sufficiently small pixel value difference S(d) to substantially zero, and thus a sharp synthetic image Comp is obtained.

When the average value AvrS of the pixel value differences is positive, it is considered that smoothing is performed in a direction closer to the peak close to 0, in which smoothing has worked well, as the pixel value difference S(d) in which a positive and a negative have been taken into consideration becomes a smaller value (a larger value in the negative direction), and thus it is necessary to increase the value of the synthesis weight α(d) corresponding to the smoothed image with a smaller pixel value difference S(d) in which a positive and a negative have been taken into consideration. In this case, the functions in FIG. 14 should be inverted right and left about the origin.

In FIG. 14, the threshold of the step function and the position of the inflection point of the logistic function are on the negative side (left side) relative to the position at which S(d) is 0, but the same may be at the same position at which S(d) is 0, or may be on the positive side (right side) relative to the position at which S(d) is 0. In addition, the function A may be another function. By applying the normalization constant k to the function A such that the sum of the synthesis weights α(d) becomes 1, the synthesis weights α(d) can be acquired based on the pixel value differences S(d) and the average value AvrS of the pixel value differences through the function A.

Here, as shown in FIG. 15, a step function, a linear function, or a logistic function similar to the above can also be used as the function B that gives the addition weight β. Specifically, the synthetic image Comp is conceivably further distorted from the image In to be processed by smoothing as the absolute value of the difference between the pixel value of the pixel of the image In to be processed and the pixel value of the pixel at the corresponding position in the synthetic image Comp increases. Therefore, when the absolute value of the difference between the pixel value of the pixel of the image In to be processed and the pixel value of the pixel of the synthetic image Comp is small, heavily weighted addition of the synthetic image Comp is performed, and when the absolute value of the difference between the pixel value of the pixel of the image In to be processed and the pixel value of the pixel of the synthetic image Comp is large, heavily weighted addition of the image In to be processed is performed such that the result of the synthetic image Comp, which is the result of smoothing, can be fed back for the image In to be processed. The nature of the function is the same as that in the case of the synthesis weights α(d) shown in FIG. 14, and thus description thereof is omitted. Note that functions in FIG. 15 have shapes obtained by inverting the functions in FIG. 14 right and left.

While the smoothing filters F(d) perform smoothing between the pixel value of the pixel at the position of interest and the pixel values of the pixels on the line segment that extends centered on the position of interest in each of the aforementioned first to third embodiments, the present invention is not restricted to this. According to the present invention, the smoothing filters F(d) may perform smoothing between the pixel value of the pixel at the position of interest and the pixel values of pixels located on two line segments that extend in different directions, centered on the position of interest. In this case, the smoothing filters F(d) accommodate to smoothing of the polygonal line structure of the subject S having the position of interest at the corner. Alternatively, the smoothing filters F(d) may perform smoothing between the pixel value of the pixel at the position of interest and the pixel values of pixels located on a curve that extends from the position of interest. In this case, the smoothing filters F(d) accommodate to smoothing of the curve structure of the subject S that passes through the position of interest. Alternatively, isotropic smoothing filters F(d) that perform smoothing without smoothing in a specific direction may be used. Furthermore, while each coefficient included in the smoothing filters F(d) is constant irrespective of a distance from the position of interest, the pixel value of a pixel closer to the position of interest may be more emphasized (more heavily weighted) to perform smoothing. In addition, the shape of each of the smoothing filters F(d) is not limited to a square filter of n rows and n columns, but may be a rectangular filter of m rows and n columns or a circular filter, for example.

While the example in which the image processing apparatus 100, 200, or 300 includes a PC has been shown in each of the aforementioned first to third embodiments, the present invention is not restricted to this. According to the present invention, the image processing apparatuses 100, 200, and 300 may be a collection of electronic components (semiconductors such as CPUs) attached to a board. In this case, a cartridge-like board may be incorporated in the X-ray imaging apparatus 101 or the low-like camera 301, or the board and the X-ray imaging apparatus 101 or the low-light camera 301 may be connected via wire or wirelessly to each other and be attached.

While the frequency analysis and frequency synthesis performed by the band-limited image processor 20 include so-called Laplacian pyramid processing performed in combination of processing for causing the average value of the pixel values of the four pixels of 2 rows and 2 columns in the input image In1 to correspond to the pixel value of one pixel, processing for causing the pixel value of one pixel to correspond to the pixel values of the four pixels of 2 rows and 2 columns, and processing for taking the differences between them in the aforementioned second embodiment, the present invention is not restricted to this. According to the present invention, the frequency analysis and frequency synthesis performed by the band-limited image processor 20 may include limiting the band of the input image In1 by wavelet transformation, decomposing the image for each frequency, and merging again the images, for example. Note that the wavelet transformation is processing for decomposing the pixel values of an image by a set of wave packets (blocks of short waves) having portions that vibrate only in a predetermined range.

While the example in which the image processing apparatus 300 having the same structure as that of the first embodiment is used for the low-light camera 301 has been shown in the aforementioned third embodiment, the present invention is not restricted to this. The image processing apparatus 300 according to the third embodiment may include the same band-limited image processor 20 as that of the second embodiment. In this case, the band-limited image processor 20 removes noise for each sine wave component corresponding to the frequency ωj from the image acquired by the low-light camera 301 to perform smoothing, and merges the images from which the noise has been removed to acquire the output image Out1. Furthermore, the image processing apparatus 300 is not limited to the low-light camera 301, but may be widely used for cameras that acquire images as image data (pixel value for each pixel). In addition, an amplifier that amplifies light incident from the imaging optical system 81 and sends it toward the imaging device 82 may be provided between the imaging optical system 81 and the imaging device 82. The amplifier includes an image intensifier, for example.

While the additive synthetic image generation processing and the synthesis weight acquisition processing are described using flowcharts in a "flow-driven manner" for the convenience of illustration in each of the aforementioned first to third embodiments, the present invention is not restricted to this. The additive synthetic image generation processing and the synthesis weight acquisition processing may be performed in an "event-driven manner" in which the processing is performed on an event basis. In this case, the processing may be performed in a complete event-driven manner or in a combination of an event-driven manner and a flow-driven manner. Furthermore, similarly, the band-by-band additive synthetic image acquisition/merging processing shown in the second embodiment may be performed in a flow-driven manner, in an event-driven manner, or in a combination of an event-driven manner and a flow-driven manner.

DESCRIPTION OF REFERENCE NUMERALS

20: band-limited image processor
21: image smoother
22: pixel value difference acquirer
23: synthesis weight acquirer
24: synthetic image acquirer
25: additive synthetic image generator
100, 200, 300: image processing apparatus

The invention claimed is:

1. An image processing apparatus comprising:
   an image smoother for acquiring pixel values of respective pixels of a plurality of smoothed images from a pixel value corresponding to luminance or chromaticity of each pixel of an image to be processed, using a plurality of smoothing filters for smoothing noise components for the each pixel of the image to be processed, the plurality of smoothing filters being different from each other;
   a pixel value difference acquirer for acquiring pixel value differences between the pixel value of the each pixel of the image to be processed and the pixel values of the respective pixels at corresponding positions in the plurality of smoothed images, which are zero, positive and/or negative differences in the pixel values corresponding to the luminance or the chromaticity of the each pixel for each of the plurality of smoothing filters;
   a synthesis weight acquirer for acquiring synthesis weights used for weighting to combine the pixel values of the respective pixels of the plurality of smoothed images, based on a plurality of the pixel value differences; and
   a synthetic image acquirer that is operable to perform weighted synthesis on the respective pixels of the plurality of smoothed images based on the synthesis weights to acquire a synthetic image.

2. The image processing apparatus according to claim 1, wherein the synthesis weight acquirer acquires an average value of the plurality of the pixel value differences, which are zero, positive and/or negative, and acquires a plurality of the synthesis weights corresponding to the each pixel based on the plurality of the pixel value differences and the average value of the pixel value differences.

3. The image processing apparatus according to claim 2, wherein when it is defined that the pixel value differences increase from a negative toward a positive, the synthesis weight acquirer is operable to perform control of increasing a synthesis weight of a smoothed image corresponding to a smaller pixel value difference among the plurality of the pixel value differences for the each pixel when the average value of the pixel value differences is positive, and is operable to perform control of increasing a synthesis weight of a smoothed image corresponding to a larger pixel value difference among the plurality of the pixel value differences for the each pixel when the average value of the pixel value differences is negative.

4. The image processing apparatus according to claim 1, further comprising an additive synthetic image generator that is operable to perform weighted addition of the pixel value of the each pixel of the image to be processed and a pixel value of each pixel at a corresponding position in the synthetic image for the each pixel and is operable to perform synthesis to acquire an additive synthetic image.

5. The image processing apparatus according to claim 4, wherein the additive synthetic image generator acquires an addition weight corresponding to the each pixel based on the pixel value of the each pixel of the image to be processed and the pixel value of the each pixel at the corresponding position in the synthetic image to acquire the additive synthetic image based on the addition weight when performing the weighted addition.

6. The image processing apparatus according to claim 1, further comprising a band-limited image processor that is operable to perform frequency analysis on an input image to acquire a plurality of images subjected to band limitation, in which only images containing specific frequencies are extracted, for respective frequencies and is operable to perform frequency synthesis to merge again the plurality of images divided for the respective frequencies, and for acquiring an output image on which the frequency synthesis has been performed, wherein
 the band-limited image processor is operable to perform the frequency analysis on the image to be processed as the input image to acquire the image to be processed, subjected to the band limitation, acquires the synthetic image subjected to the band limitation and the weighted synthesis based on the pixel value differences, which are zero, positive and/or negative, for the each pixel, is operable to perform the frequency synthesis on images based on the synthetic image subjected to the band limitation and the weighted synthesis, and acquires the output image.

\* \* \* \* \*